(12) United States Patent
Seki

(10) Patent No.: US 10,716,790 B2
(45) Date of Patent: Jul. 21, 2020

(54) METHOD FOR TREATING CANCER BY COMBINED USE

(71) Applicant: DAIICHI SANKYO COMPANY, LIMITED, Tokyo (JP)

(72) Inventor: Takahiko Seki, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 0 days.

(21) Appl. No.: 15/487,738

(22) Filed: Apr. 14, 2017

(65) Prior Publication Data

US 2017/0216302 A1 Aug. 3, 2017

Related U.S. Application Data

(63) Continuation of application No. PCT/JP2016/054822, filed on Feb. 19, 2016.

(30) Foreign Application Priority Data

Feb. 20, 2015 (JP) ................................ 2015-032201

(51) Int. Cl.
A61K 31/5377 (2006.01)
A61K 31/4439 (2006.01)

(52) U.S. Cl.
CPC ...... *A61K 31/5377* (2013.01); *A61K 31/4439* (2013.01)

(58) Field of Classification Search
None
See application file for complete search history.

(56) References Cited

U.S. PATENT DOCUMENTS

| | | | |
|---|---|---|---|
| 8,357,690 B2 | 1/2013 | Armstrong et al. | |
| 2009/0123418 A1 | 5/2009 | James | |
| 2009/0131426 A1 | 5/2009 | Bhagwat et al. | |
| 2010/0104567 A1 | 4/2010 | Shiotsu et al. | |
| 2011/0251252 A1* | 10/2011 | Wang | G01N 33/57426 514/409 |
| 2012/0264738 A1 | 10/2012 | Sugimoto et al. | |
| 2015/0210707 A1 | 7/2015 | Yoshida et al. | |

FOREIGN PATENT DOCUMENTS

| | | |
|---|---|---|
| EP | 0 959 132 A2 | 11/1999 |
| EP | 1 712 235 A2 | 10/2006 |
| WO | WO 1998/017808 A1 | 4/1998 |
| WO | WO 2006/024837 A1 | 3/2006 |
| WO | WO 2006/032631 A1 | 3/2006 |
| WO | WO 2006/091646 A2 | 8/2006 |
| WO | WO 2006/136606 A2 | 12/2006 |
| WO | WO 2007/104664 A1 | 9/2007 |
| WO | WO 2007/104714 A1 | 9/2007 |
| WO | WO 2007/109120 A2 | 9/2007 |
| WO | WO 2007/115289 A2 | 10/2007 |
| WO | WO 2008/005266 A2 | 1/2008 |
| WO | WO 2008/034736 A2 | 3/2008 |
| WO | WO 2008/036168 A2 | 3/2008 |
| WO | WO 2008/055812 A1 | 5/2008 |
| WO | WO 2008/111441 A1 | 9/2008 |
| WO | WO 2008/119741 A2 | 10/2008 |
| WO | WO 2008/141917 A1 | 11/2008 |
| WO | WO 2008/141975 A1 | 11/2008 |
| WO | WO 2009/061446 A1 | 5/2009 |
| WO | WO 2009/077357 A1 | 6/2009 |
| WO | WO 2009/080488 A1 | 7/2009 |
| WO | WO 2010/028862 A1 | 3/2010 |
| WO | WO 2010/031713 A1 | 3/2010 |
| WO | WO 2010/084097 A1 | 7/2010 |
| WO | WO 2010/091979 A1 | 8/2010 |
| WO | WO 2010/094622 A1 | 8/2010 |
| WO | WO 2010/111172 A1 | 9/2010 |
| WO | WO 2010/121995 A1 | 10/2010 |
| WO | WO 2010/132787 A1 | 11/2010 |
| WO | WO 2011/127058 A1 | 10/2011 |
| WO | WO 2012/121361 A1 | 9/2012 |
| WO | WO 2012/155066 A1 | 11/2012 |
| WO | WO 2013/139724 A1 | 9/2013 |
| WO | WO 2014/020502 A1 | 2/2014 |
| WO | WO 2014/038606 A1 | 3/2014 |
| WO | WO 2014/055397 A1 | 4/2014 |
| WO | WO 2014/107713 A1 | 7/2014 |
| WO | WO 2015/000945 A1 | 1/2015 |
| WO | WO 2015/070224 A2 | 5/2015 |

OTHER PUBLICATIONS

Chen et al., "Identification and Characterization of a Potent FLT3 Inhibitor," *Blood Journal*, (2013), 122:5027.
Ding et al., "Structure-Based Design of Potent Non-Peptide MDM2 Inhibitors," *J. Am. Chem. Soc.*, (2005), 127:10130-10131.
Ding et al., "Structure-Based Design of Spiro-oxindoles as Potent, Specific Small-Molecule Inhibitors of the MDM2-p53 Interaction," *J. Med. Chem.*, (2006), 49:3432-3435.
Hardcastle et al., "Small-Molecule Inhibitors of the MDM2-p53 Protein-Protein Interaction Based on an Isoindolinone Scaffold," *J. Med. Chem.*, (2006), 49:6209-6221.
Kojima, "Concurrent Inhibition of FLT3 and MDM2 as a Novel Treatment Strategy for Mutant FLT3 AML," *Hematology*, (2011), 62(2):220-225.

(Continued)

*Primary Examiner* — James D. Anderson
*Assistant Examiner* — Stephanie K Springer
(74) *Attorney, Agent, or Firm* — Dorsey & Whitney LLP

(57) ABSTRACT

It is intended to provide a medicament and a method for treating cancer comprising a compound having MDM2 inhibiting activity and a compound having FLT3 inhibiting activity in combination. The present invention provides a medicament comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydro-dispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof in combination, and a treatment method using these compounds or salts in combination.

5 Claims, 2 Drawing Sheets

Specification includes a Sequence Listing.

(56) References Cited

OTHER PUBLICATIONS

Kojima et al., "Selective FLT3 inhibitor Fl-700 neutralizes Mcl-1 and enhances p53-mediated apoptosis in AML cells with activating mutations of FLT3 through Mcl-1/Noxa axis," *Leukemia*, (2010), 24:33-43.
Kondo, "Hematopoietic Stem Cell Transplantation for AML with FLT3-ITD," *Hematology*, (2012), 65(5):659-664.
Prescott et al., "Emerging FMS-like tyrosine kinase 3 inhibitors for the treatment of acute myelogenous leukemia," *Expert Opinion on Emerging Drugs*, (2011), 16(3):407-423.
Yu et al., "Potent and Orally Active Small-Molecule Inhibitors of the MDM2-p53 Interaction," *J. Med. Chem.*, (2009), 52:7970-7973.
Levis, "Quizartinib for the treatment of FLT3/ITD acute myeloid leukemia," *Future Oncology*, (2014), 10(9):1571-1579.
Zarrinkar, et al., "AC220 is a uniquely potent and selective inhibitor of FLT3 for the treatment of acute myeloid leukemia (AML)," *Blood*, (2009), 114(14):2984-2992.
Yokoyama et al., "Synergy between Angiostatin and Endostatin: Inhibition of Ovarian Cancer Growth," *Cancer Research*, (2000), 60:2190-2196.

* cited by examiner

[Figure 1-1]
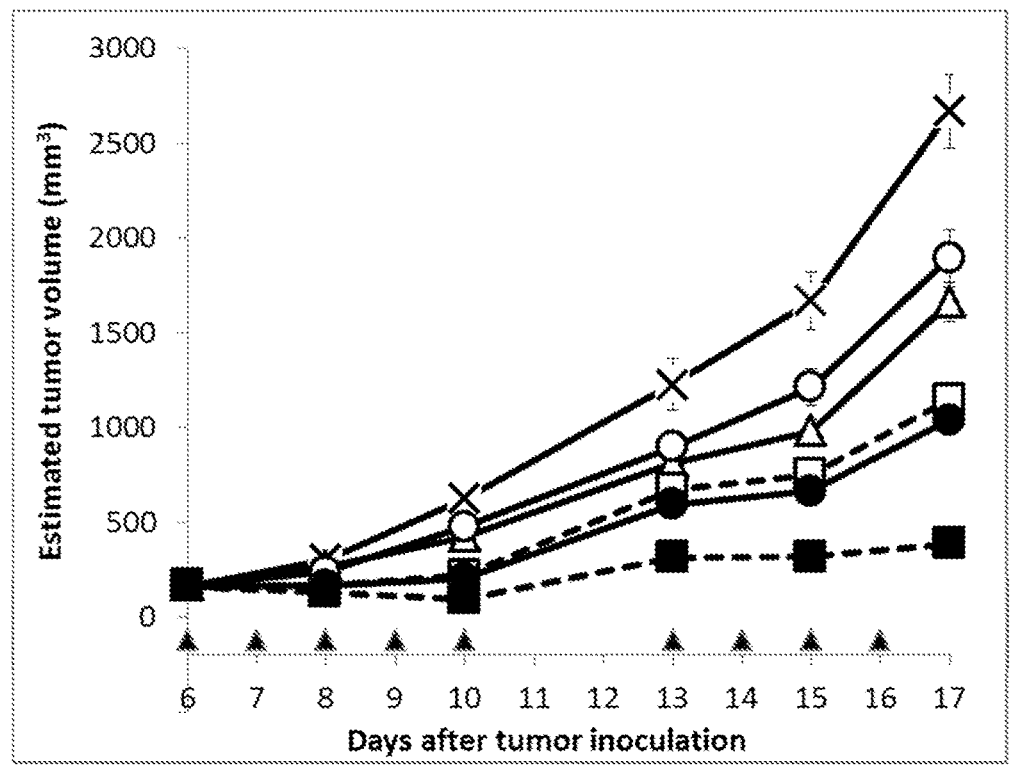
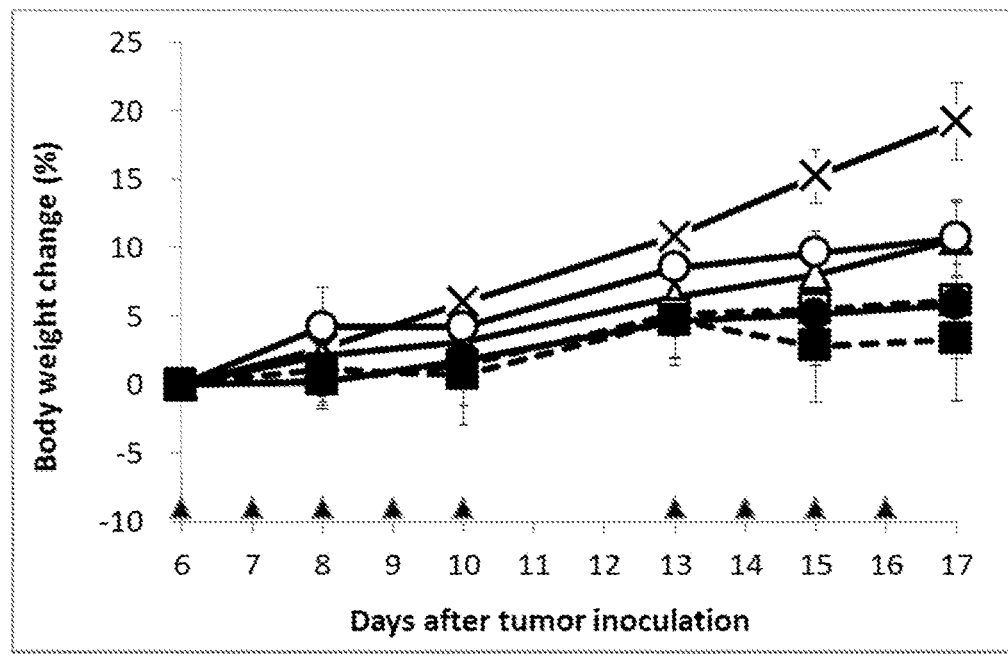

[Figure 1-2]
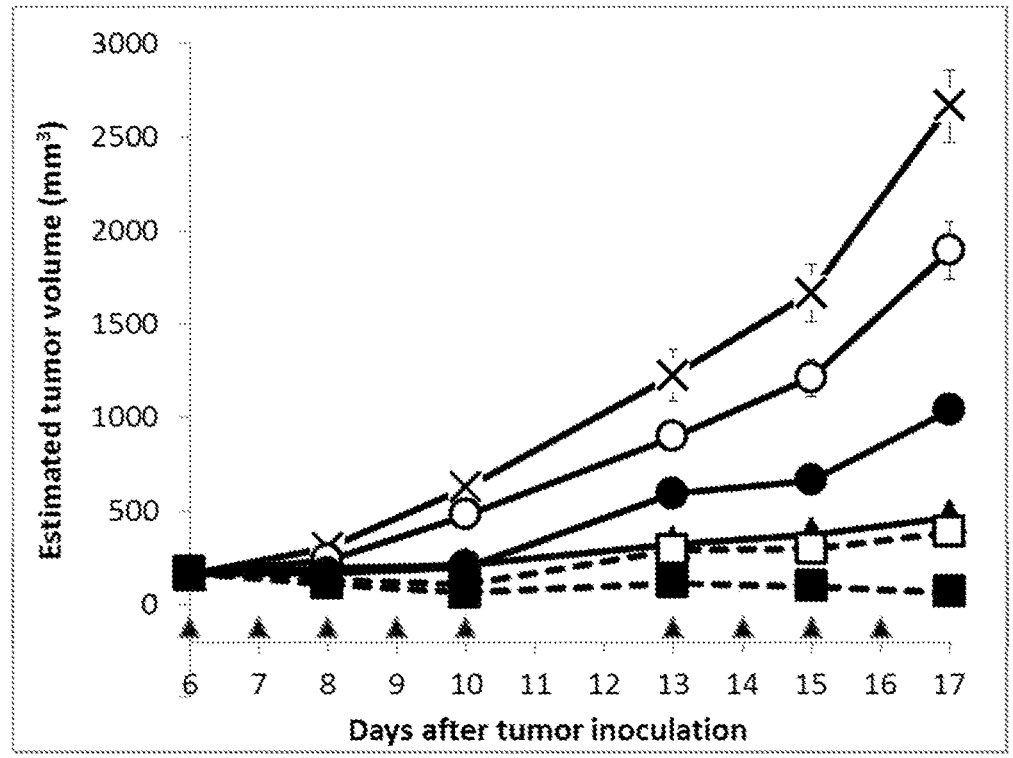
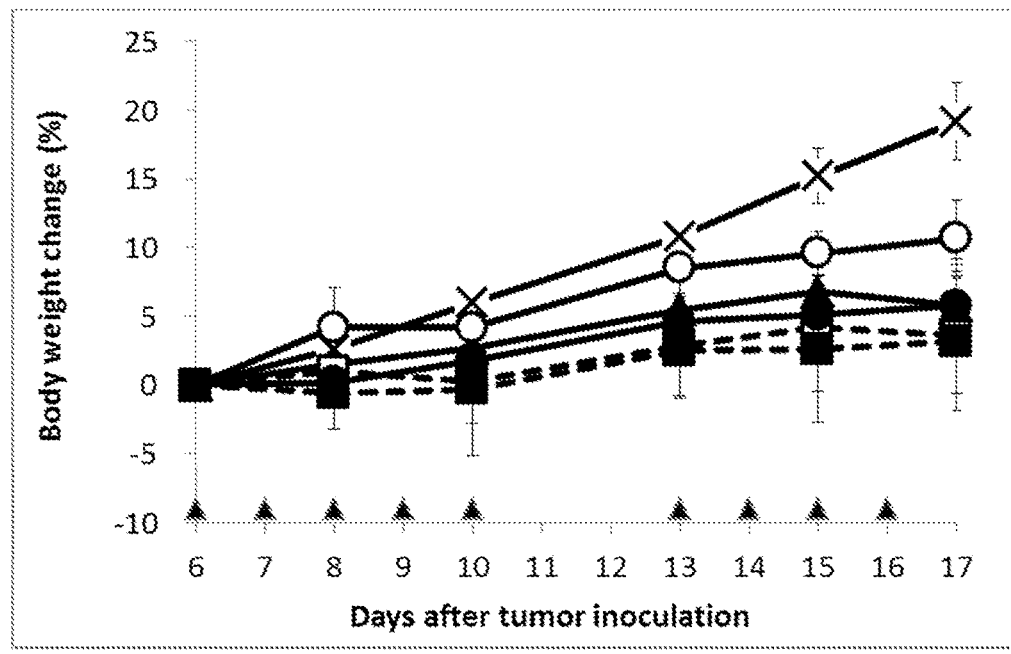

```
                        SEQUENCE LISTING

<160> NUMBER OF SEQ ID NOS: 4

<210> SEQ ID NO 1
<211> LENGTH: 3848
<212> TYPE: DNA
<213> ORGANISM: Homo sapiens
<220> FEATURE:
<221> NAME/KEY: misc_feature
<223> OTHER INFORMATION: FLT3 mRNA encoding FLT3 protein (SEQ ID NO.2)
<220> FEATURE:
<221> NAME/KEY: CDS
<222> LOCATION: (83)..(3064)

<400> SEQUENCE: 1
acctgcagcg cgaggcgcgc cgctccaggc ggcatcgcag ggctgggccg gcgcggcctg      60
gggaccccgg gctccggagg cc atg ccg gcg ttg gcg cgc gac ggc ggc cag     112
                         Met Pro Ala Leu Ala Arg Asp Gly Gly Gln
                          1               5                  10 ctg ccg ctg ctc gtt gtt ttt tct gca atg ata ttt ggg act att aca    160
Leu Pro Leu Leu Val Val Phe Ser Ala Met Ile Phe Gly Thr Ile Thr
                15                  20                  25 aat caa gat ctg cct gtg atc aag tgt gtt tta atc aat cat aag aac    208
Asn Gln Asp Leu Pro Val Ile Lys Cys Val Leu Ile Asn His Lys Asn
         30                  35                  40 aat gat tca tca gtg ggg aag tca tca tat ccc atg gta tca gaa        256
Asn Asp Ser Ser Val Gly Lys Ser Ser Ser Tyr Pro Met Val Ser Glu
     45                  50                  55 tcc ccg gaa gac ctc ggg tgt gcg ttg aga ccc cag agc tca ggg aca    304
Ser Pro Glu Asp Leu Gly Cys Ala Leu Arg Pro Gln Ser Ser Gly Thr
 60                  65                  70 gtg tac gaa gct gcc gct gtg gaa gtg gat gta tct gct tcc atc aca    352
Val Tyr Glu Ala Ala Ala Val Glu Val Asp Val Ser Ala Ser Ile Thr
75                  80                  85                  90 ctg caa gtg ctg gtc gac gcc cca ggg aac att tcc tgt ctc tgg gtc    400
Leu Gln Val Leu Val Asp Ala Pro Gly Asn Ile Ser Cys Leu Trp Val
                 95                 100                 105 ttt aag cac agc tcc ctg aat tgc cag cca cat ttt gat tta caa aac    448
Phe Lys His Ser Ser Leu Asn Cys Gln Pro His Phe Asp Leu Gln Asn
            110                 115                 120
```

```
aga gga gtt gtt tcc atg gtc att ttg aaa atg aca gaa acc caa gct      496
Arg Gly Val Val Ser Met Val Ile Leu Lys Met Thr Glu Thr Gln Ala
        125                 130                 135 gga gaa tac cta ctt ttt att cag agt gaa gct acc aat tac aca ata      544
Gly Glu Tyr Leu Leu Phe Ile Gln Ser Glu Ala Thr Asn Tyr Thr Ile
        140                 145                 150 ttg ttt aca gtg agt ata aga aat acc ctg ctt tac aca tta aga aga      592
Leu Phe Thr Val Ser Ile Arg Asn Thr Leu Leu Tyr Thr Leu Arg Arg
155                 160                 165                 170 cct tac ttt aga aaa atg gaa aac cag gac gcc ctg gtc tgc ata tct      640
Pro Tyr Phe Arg Lys Met Glu Asn Gln Asp Ala Leu Val Cys Ile Ser
                175                 180                 185 gag agc gtt cca gag ccg atc gtg gaa tgg gtg ctt tgc gat tca cag      688
Glu Ser Val Pro Glu Pro Ile Val Glu Trp Val Leu Cys Asp Ser Gln
                190                 195                 200 ggg gaa agc tgt aaa gaa gaa agt cca gct gtt gtt aaa aag gag gaa      736
Gly Glu Ser Cys Lys Glu Glu Ser Pro Ala Val Val Lys Lys Glu Glu
        205                 210                 215 aaa gtg ctt cat gaa tta ttt ggg acg gac ata agg tgc tgt gcc aga      784
Lys Val Leu His Glu Leu Phe Gly Thr Asp Ile Arg Cys Cys Ala Arg
220                 225                 230 aat gaa ctg ggc agg gaa tgc acc agg ctg ttc aca ata gat cta aat      832
Asn Glu Leu Gly Arg Glu Cys Thr Arg Leu Phe Thr Ile Asp Leu Asn
235                 240                 245                 250 caa act cct cag acc aca ttg cca caa tta ttt ctt aaa gta ggg gaa      880
Gln Thr Pro Gln Thr Thr Leu Pro Gln Leu Phe Leu Lys Val Gly Glu
                255                 260                 265 ccc tta tgg ata agg tgc aaa gct gtt cat gtg aac cat gga ttc ggg      928
Pro Leu Trp Ile Arg Cys Lys Ala Val His Val Asn His Gly Phe Gly
                270                 275                 280 ctc acc tgg gaa tta gaa aac aaa gca ctc gag gag ggc aac tac ttt      976
Leu Thr Trp Glu Leu Glu Asn Lys Ala Leu Glu Glu Gly Asn Tyr Phe
        285                 290                 295 gag atg agt acc tat tca aca aac aga act atg ata cgg att ctg ttt     1024
Glu Met Ser Thr Tyr Ser Thr Asn Arg Thr Met Ile Arg Ile Leu Phe
        300                 305                 310 gct ttt gta tca tca gtg gca aga aac gac acc gga tac tac act tgt     1072
Ala Phe Val Ser Ser Val Ala Arg Asn Asp Thr Gly Tyr Tyr Thr Cys
315                 320                 325                 330 tcc tct tca aag cat ccc agt caa tca gct ttg gtt acc atc gta gaa     1120
Ser Ser Ser Lys His Pro Ser Gln Ser Ala Leu Val Thr Ile Val Glu
                335                 340                 345 aag gga ttt ata aat gct acc aat tca agt gaa gat tat gaa att gac     1168
Lys Gly Phe Ile Asn Ala Thr Asn Ser Ser Glu Asp Tyr Glu Ile Asp
                350                 355                 360 caa tat gaa gag ttt tgt ttt tct gtc agg ttt aaa gcc tac cca caa     1216
Gln Tyr Glu Glu Phe Cys Phe Ser Val Arg Phe Lys Ala Tyr Pro Gln
        365                 370                 375 atc aga tgt acg tgg acc ttc tct cga aaa tca ttt cct tgt gag caa     1264
Ile Arg Cys Thr Trp Thr Phe Ser Arg Lys Ser Phe Pro Cys Glu Gln
380                 385                 390 aag ggt ctt gat aac gga tac agc ata tcc aag ttt tgc aat cat aag     1312
Lys Gly Leu Asp Asn Gly Tyr Ser Ile Ser Lys Phe Cys Asn His Lys
395                 400                 405                 410 cac cag cca gga gaa tat ata ttc cat gca gaa aat gat gat gcc caa     1360
His Gln Pro Gly Glu Tyr Ile Phe His Ala Glu Asn Asp Asp Ala Gln
                415                 420                 425 ttt acc aaa atg ttc acg ctg aat ata aga agg aaa cct caa gtg ctc     1408
Phe Thr Lys Met Phe Thr Leu Asn Ile Arg Arg Lys Pro Gln Val Leu
        430                 435                 440
```

-continued

| | |
|---|---|
| gca gaa gca tcg gca agt cag gcg tcc tgt ttc tcg gat gga tac cca<br>Ala Glu Ala Ser Ala Ser Gln Ala Ser Cys Phe Ser Asp Gly Tyr Pro<br>          445                  450                  455 | 1456 |
| tta cca tct tgg acc tgg aag aag tgt tca gac aag tct ccc aac tgc<br>Leu Pro Ser Trp Thr Trp Lys Lys Cys Ser Asp Lys Ser Pro Asn Cys<br>460                        465                  470 | 1504 |
| aca gaa gag atc aca gaa gga gtc tgg aat aga aag gct aac aga aaa<br>Thr Glu Glu Ile Thr Glu Gly Val Trp Asn Arg Lys Ala Asn Arg Lys<br>475                  480                  485                  490 | 1552 |
| gtg ttt gga cag tgg gtg tcg agc agt act cta aac atg agt gaa gcc<br>Val Phe Gly Gln Trp Val Ser Ser Ser Thr Leu Asn Met Ser Glu Ala<br>                   495                  500                  505 | 1600 |
| ata aaa ggg ttc ctg gtc aag tgc tgt gca tac aat tcc ctt ggc aca<br>Ile Lys Gly Phe Leu Val Lys Cys Cys Ala Tyr Asn Ser Leu Gly Thr<br>510                      515                  520 | 1648 |
| tct tgt gag acg atc ctt tta aac tct cca ggc ccc ttc cct ttc atc<br>Ser Cys Glu Thr Ile Leu Leu Asn Ser Pro Gly Pro Phe Pro Phe Ile<br>         525                  530                  535 | 1696 |
| caa gac aac atc tca ttc tat gca aca att ggt gtt tgt ctc ctc ttc<br>Gln Asp Asn Ile Ser Phe Tyr Ala Thr Ile Gly Val Cys Leu Leu Phe<br>540                      545                  550 | 1744 |
| att gtc gtt tta acc ctg cta att tgt cac aag tac aaa aag caa ttt<br>Ile Val Val Leu Thr Leu Leu Ile Cys His Lys Tyr Lys Lys Gln Phe<br>555                  560                  565                  570 | 1792 |
| agg tat gaa agc cag cta cag atg gta cag gtg acc ggc tcc tca gat<br>Arg Tyr Glu Ser Gln Leu Gln Met Val Gln Val Thr Gly Ser Ser Asp<br>                   575                  580                  585 | 1840 |
| aat gag tac ttc tac gtt gat ttc aga gaa tat gaa tat gat ctc aaa<br>Asn Glu Tyr Phe Tyr Val Asp Phe Arg Glu Tyr Glu Tyr Asp Leu Lys<br>590                      595                  600 | 1888 |
| tgg gag ttt cca aga gaa aat tta gag ttt ggg aag gta cta gga tca<br>Trp Glu Phe Pro Arg Glu Asn Leu Glu Phe Gly Lys Val Leu Gly Ser<br>         605                  610                  615 | 1936 |
| ggt gct ttt gga aaa gtg atg aac gca aca gct tat gga att agc aaa<br>Gly Ala Phe Gly Lys Val Met Asn Ala Thr Ala Tyr Gly Ile Ser Lys<br>620                      625                  630 | 1984 |
| aca gga gtc tca atc cag gtt gcc gtc aaa atg ctg aaa gaa aaa gca<br>Thr Gly Val Ser Ile Gln Val Ala Val Lys Met Leu Lys Glu Lys Ala<br>635                      640                  645                  650 | 2032 |
| gac agc tct gaa aga gag gca ctc atg tca gaa ctc aag atg atg acc<br>Asp Ser Ser Glu Arg Glu Ala Leu Met Ser Glu Leu Lys Met Met Thr<br>                   655                  660                  665 | 2080 |
| cag ctg gga agc cac gag aat att gtg aac ctg ctg ggg gcg tgc aca<br>Gln Leu Gly Ser His Glu Asn Ile Val Asn Leu Leu Gly Ala Cys Thr<br>670                      675                  680 | 2128 |
| ctg tca gga cca att tac ttg att ttt gaa tac tgt tgc tat ggt gat<br>Leu Ser Gly Pro Ile Tyr Leu Ile Phe Glu Tyr Cys Cys Tyr Gly Asp<br>         685                  690                  695 | 2176 |
| ctt ctc aac tat cta aga agt aaa aga gaa aaa ttt cac agg act tgg<br>Leu Leu Asn Tyr Leu Arg Ser Lys Arg Glu Lys Phe His Arg Thr Trp<br>700                      705                  710 | 2224 |
| aca gag att ttc aag gaa cac aat ttc agt ttt tac ccc act ttc caa<br>Thr Glu Ile Phe Lys Glu His Asn Phe Ser Phe Tyr Pro Thr Phe Gln<br>715                      720                  725                  730 | 2272 |
| tca cat cca aat tcc agc atg cct ggt caa aga gaa gtt cag ata cac<br>Ser His Pro Asn Ser Ser Met Pro Gly Ser Arg Glu Val Gln Ile His<br>                   735                  740                  745 | 2320 |
| ccg gac tcg gat caa atc tca ggg ctt cat ggg aat tca ttt cac tct<br>Pro Asp Ser Asp Gln Ile Ser Gly Leu His Gly Asn Ser Phe His Ser | 2368 |

```
                750             755             760
gaa gat gaa att gaa tat gaa aac caa aaa agg ctg gaa gag gag gag       2416
Glu Asp Glu Ile Glu Tyr Glu Asn Gln Lys Arg Leu Glu Glu Glu Glu
            765             770             775 gac ttg aat gtg ctt aca ttt gaa gat ctt ctt tgc ttt gca tat caa       2464
Asp Leu Asn Val Leu Thr Phe Glu Asp Leu Leu Cys Phe Ala Tyr Gln
            780             785             790 gtt gcc aaa gga atg gaa ttt ctg gaa ttt aag tcg tgt gtt cac aga       2512
Val Ala Lys Gly Met Glu Phe Leu Glu Phe Lys Ser Cys Val His Arg
795             800             805             810 gac ctg gcc gcc agg aac gtg ctt gtc acc cac ggg aaa gtg gtg aag       2560
Asp Leu Ala Ala Arg Asn Val Leu Val Thr His Gly Lys Val Val Lys
            815             820             825 ata tgt gac ttt gga ttg gct cga gat atc atg agt gat tcc aac tat       2608
Ile Cys Asp Phe Gly Leu Ala Arg Asp Ile Met Ser Asp Ser Asn Tyr
            830             835             840 gtt gtc agg ggc aat gcc cgt ctg cct gta aaa tgg atg gcc ccc gaa       2656
Val Val Arg Gly Asn Ala Arg Leu Pro Val Lys Trp Met Ala Pro Glu
            845             850             855 agc ctg ttt gaa ggc atc tac acc att aag agt gat gtc tgg tca tat       2704
Ser Leu Phe Glu Gly Ile Tyr Thr Ile Lys Ser Asp Val Trp Ser Tyr
            860             865             870 gga ata tta ctg tgg gaa atc ttc tca ctt ggt gtg aat cct tac cct       2752
Gly Ile Leu Leu Trp Glu Ile Phe Ser Leu Gly Val Asn Pro Tyr Pro
875             880             885             890 ggc att ccg gtt gat gct aac ttc tac aaa ctg att caa aat gga ttt       2800
Gly Ile Pro Val Asp Ala Asn Phe Tyr Lys Leu Ile Gln Asn Gly Phe
            895             900             905 aaa atg gat cag cca ttt tat gct aca gaa gaa ata tac att ata atg       2848
Lys Met Asp Gln Pro Phe Tyr Ala Thr Glu Glu Ile Tyr Ile Ile Met
            910             915             920 caa tcc tgc tgg gct ttt gac tca agg aaa cgg cca tcc ttc cct aat       2896
Gln Ser Cys Trp Ala Phe Asp Ser Arg Lys Arg Pro Ser Phe Pro Asn
            925             930             935 ttg act tcg ttt tta gga tgt cag ctg gca gat gca gaa gaa gcg atg       2944
Leu Thr Ser Phe Leu Gly Cys Gln Leu Ala Asp Ala Glu Glu Ala Met
            940             945             950 tat cag aat gtg gat ggc cgt gtt tcg gaa tgt cct cac acc tac caa       2992
Tyr Gln Asn Val Asp Gly Arg Val Ser Glu Cys Pro His Thr Tyr Gln
955             960             965             970 aac agg cga cct ttc agc aga gag atg gat ttg ggg cta ctc tct ccg       3040
Asn Arg Arg Pro Phe Ser Arg Glu Met Asp Leu Gly Leu Leu Ser Pro
            975             980             985 cag gct cag gtc gaa gat tcg tag aggaacaatt tagttttaag gacttcatcc     3094
Gln Ala Gln Val Glu Asp Ser
            990 ctccacctat ccctaacagg ctgtagatta ccaaaacaag attaatttca tcactaaaag    3154 aaaatctatt atcaactgct gcttcaccag acttttctct agaagctgtc tgcgtttact    3214 cttgttttca aagggacttt tgtaaaatca aatcatcctg tcacaaggca ggaggagctg    3274 ataatgaact ttattggagc attgatctgc atccaaggcc ttctcaggct ggcttgagtg    3334 aattgtgtac ctgaagtaca gtatattctt gtaaatacat aaaacaaaag cattttgcta    3394 aggagaagct aatatgattt tttaagtcta tgttttaaaa taatatgtaa attttttcagc   3454 tatttagtga tatattttat gggtgggaat aaaattttcta ctacagaatt gcccattatt   3514 gaattattta catggtataa ttagggcaag tcttaactgg agttcacgaa ccccctgaaa    3574 ttgtgcaccc atagccacct acacattcct tccagagcac gtgtgctttt accccaagat    3634
```

-continued

```
acaaggaatg tgtaggcagc tatggttgtc acagcctaag atttctgcaa caacaggggt    3694
tgtattgggg gaagtttata atgaataggt gttctaccat aaagagtaat acatcaccta    3754
gacactttgg cggccttccc agactcaggg ccagtcagaa gtaacatgga ggattagtat    3814
tttcaataaa gttactcttg tccccacaaa aaaa                                3848
```

<210> SEQ ID NO 2
<211> LENGTH: 993
<212> TYPE: PRT
<213> ORGANISM: Homo sapiens

<400> SEQUENCE: 2

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335
```

```
Ser Gln Ser Ala Leu Val Thr Ile Val Glu Lys Gly Phe Ile Asn Ala
        340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
                435                 440                 445

Gln Ala Ser Cys Phe Ser Asp Gly Tyr Pro Leu Pro Ser Trp Thr Trp
        450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
        530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
        580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
        610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
                675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750
```

```
Ser Gly Leu His Gly Asn Ser Phe His Ser Glu Asp Glu Ile Glu Tyr
            755                 760                 765

Glu Asn Gln Lys Arg Leu Glu Glu Glu Asp Leu Asn Val Leu Thr
770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
    850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
    930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975

Arg Glu Met Asp Leu Gly Leu Leu Ser Pro Gln Ala Gln Val Glu Asp
            980                 985                 990

Ser

<210> SEQ ID NO 3
<211> LENGTH: 2591
<212> TYPE: DNA
<213> ORGANISM: Homo sapiens
<220> FEATURE:
<221> NAME/KEY: misc_feature
<223> OTHER INFORMATION: TP53 mRNA encoding TP53 protein (SEQ ID NO:4)
<220> FEATURE:
<221> NAME/KEY: CDS
<222> LOCATION: (203)..(1384)

<400> SEQUENCE: 3
gatgggattg gggttttccc ctcccatgtg ctcaagactg gcgctaaaag ttttgagctt     60
ctcaaaagtc tagagccacc gtccagggag caggtagctg ctgggctccg ggacacttt    120 gcgttcgggc tgggagcgtg ctttccacga cggtgacacg cttccctgga ttggcagcca   180
gactgccttc cgggtcactg cc atg gag gag ccg cag tca gat cct agc gtc    232
                          Met Glu Glu Pro Gln Ser Asp Pro Ser Val
                            1               5                  10 gag ccc cct ctg agt cag gaa aca ttt tca gac cta tgg aaa cta ctt    280
Glu Pro Pro Leu Ser Gln Glu Thr Phe Ser Asp Leu Trp Lys Leu Leu
                15                  20                  25 cct gaa aac aac gtt ctg tcc ccc ttg ccg tcc caa gca atg gat gat    328
Pro Glu Asn Asn Val Leu Ser Pro Leu Pro Ser Gln Ala Met Asp Asp
            30                  35                  40
```

```
ttg atg ctg tcc ccg gac gat att gaa caa tgg ttc act gaa gac cca    376
Leu Met Leu Ser Pro Asp Asp Ile Glu Gln Trp Phe Thr Glu Asp Pro
         45                  50                  55 ggt cca gat gaa gct ccc aga atg cca gag gct gct ccc ccc gtg gcc    424
Gly Pro Asp Glu Ala Pro Arg Met Pro Glu Ala Ala Pro Pro Val Ala
 60                  65                  70 cct gca cca gca gct cct aca ccg gcg gcc cct gca cca gcc ccc tcc    472
Pro Ala Pro Ala Ala Pro Thr Pro Ala Ala Pro Ala Pro Ala Pro Ser
 75                  80                  85                  90 tgg ccc ctg tca tct tct gtc cct tcc cag aaa acc tac cag ggc agc    520
Trp Pro Leu Ser Ser Ser Val Pro Ser Gln Lys Thr Tyr Gln Gly Ser
             95                 100                 105 tac ggt ttc cgt ctg ggc ttc ttg cat tct ggg aca gcc aag tct gtg    568
Tyr Gly Phe Arg Leu Gly Phe Leu His Ser Gly Thr Ala Lys Ser Val
                110                 115                 120 act tgc acg tac tcc cct gcc ctc aac aag atg ttt tgc caa ctg gcc    616
Thr Cys Thr Tyr Ser Pro Ala Leu Asn Lys Met Phe Cys Gln Leu Ala
            125                 130                 135 aag acc tgc cct gtg cag ctg tgg gtt gat tcc aca ccc ccg ccc ggc    664
Lys Thr Cys Pro Val Gln Leu Trp Val Asp Ser Thr Pro Pro Pro Gly
    140                 145                 150 acc cgc gtc cgc gcc atg gcc atc tac aag cag tca cag cac atg acg    712
Thr Arg Val Arg Ala Met Ala Ile Tyr Lys Gln Ser Gln His Met Thr
155                 160                 165                 170 gag gtt gtg agg cgc tgc ccc cac cat gag cgc tgc tca gat agc gat    760
Glu Val Val Arg Arg Cys Pro His His Glu Arg Cys Ser Asp Ser Asp
                175                 180                 185 ggt ctg gcc cct cct cag cat ctt atc cga gtg gaa gga aat ttg cgt    808
Gly Leu Ala Pro Pro Gln His Leu Ile Arg Val Glu Gly Asn Leu Arg
            190                 195                 200 gtg gag tat ttg gat gac aga aac act ttt cga cat agt gtg gtg gtg    856
Val Glu Tyr Leu Asp Asp Arg Asn Thr Phe Arg His Ser Val Val Val
        205                 210                 215 ccc tat gag ccg cct gag gtt ggc tct gac tgt acc acc atc cac tac    904
Pro Tyr Glu Pro Pro Glu Val Gly Ser Asp Cys Thr Thr Ile His Tyr
    220                 225                 230 aac tac atg tgt aac agt tcc tgc atg ggc ggc atg aac cgg agg ccc    952
Asn Tyr Met Cys Asn Ser Ser Cys Met Gly Gly Met Asn Arg Arg Pro
235                 240                 245                 250 atc ctc acc atc atc aca ctg gaa gac tcc agt ggt aat cta ctg gga   1000
Ile Leu Thr Ile Ile Thr Leu Glu Asp Ser Ser Gly Asn Leu Leu Gly
                255                 260                 265 cgg aac agc ttt gag gtg cgt gtt tgt gcc tgt cct ggg aga gac cgg   1048
Arg Asn Ser Phe Glu Val Arg Val Cys Ala Cys Pro Gly Arg Asp Arg
            270                 275                 280 cgc aca gag gaa gag aat ctc cgc aag aaa ggg gag cct cac cac gag   1096
Arg Thr Glu Glu Glu Asn Leu Arg Lys Lys Gly Glu Pro His His Glu
        285                 290                 295 ctg ccc cca ggg agc act aag cga gca ctg ccc aac aac acc agc tcc   1144
Leu Pro Pro Gly Ser Thr Lys Arg Ala Leu Pro Asn Asn Thr Ser Ser
    300                 305                 310 tct ccc cag cca aag aag aaa cca ctg gat gga gaa tat ttc acc ctt   1192
Ser Pro Gln Pro Lys Lys Lys Pro Leu Asp Gly Glu Tyr Phe Thr Leu
315                 320                 325                 330 cag atc cgt ggg cgt gag cgc ttc gag atg ttc cga gag ctg aat gag   1240
Gln Ile Arg Gly Arg Glu Arg Phe Glu Met Phe Arg Glu Leu Asn Glu
                335                 340                 345 gcc ttg gaa ctc aag gat gcc cag gct ggg aag gag cca ggg ggg agc   1288
Ala Leu Glu Leu Lys Asp Ala Gln Ala Gly Lys Glu Pro Gly Gly Ser
            350                 355                 360
```

```
agg gct cac tcc agc cac ctg aag tcc aaa aag ggt cag tct acc tcc   1336
Arg Ala His Ser Ser His Leu Lys Ser Lys Lys Gly Gln Ser Thr Ser
            365                 370                 375 cgc cat aaa aaa ctc atg ttc aag aca gaa ggg cct gac tca gac tga   1384
Arg His Lys Lys Leu Met Phe Lys Thr Glu Gly Pro Asp Ser Asp
    380                 385                 390 cattctccac ttcttgttcc ccactgacag cctcccaccc ccatctctcc ctcccctgcc   1444
attttgggtt ttgggtcttt gaacccttgc ttgcaatagg tgtgcgtcag aagcacccag   1504
gacttccatt tgctttgtcc cggggctcca ctgaacaagt tggcctgcac tggtgttttg   1564
ttgtggggag gaggatgggg agtaggacat accagcttag attttaaggt ttttactgtg   1624
agggatgttt gggagatgta agaaatgttc ttgcagttaa gggttagttt acaatcagcc   1684
acattctagg taggggccca cttcaccgta ctaaccaggg aagctgtccc tcactgttga   1744
attttctcta acttcaaggc ccatatctgt gaaatgctgg catttgcacc tacctcacag   1804
agtgcattgt gagggttaat gaaataatgt acatctggcc ttgaaaccac ctttttattac   1864
atggggtcta gaacttgacc cccttgaggg tgcttgttcc ctctccctgt tggtcggtgg   1924
gttggtagtt tctacagttg ggcagctggt taggtagagg gagttgtcaa gtctctgctg   1984
gcccagccaa accctgtctg acaacctctt ggtgaacctt agtacctaaa aggaaatctc   2044
accccatccc acaccctgga ggatttcatc tcttgtatat gatgatctgg atccaccaag   2104
acttgtttta tgctcagggt caatttcttt ttctttttt tttttttttt ttcttttttct   2164
ttgagactgg gtctcgcttt gttgcccagg ctggagtgga gtggcgtgat cttggcttac   2224
tgcagccttt gcctccccgg ctcgagcagt cctgcctcag cctccggagt agctgggacc   2284
acaggttcat gccaccatgg ccagccaact tttgcatgtt ttgtagagat ggggtctcac   2344
agtgttgccc aggctggtct caaactcctg ggctcaggcg atccacctgt ctcagcctcc   2404
cagagtgctg ggattacaat tgtgagccac cacgtccagc tggaagggtc aacatctttt   2464
acattctgca agcacatctg cattttcacc ccacccttcc cctccttctc cctttttata   2524
tcccattttt atatcgatct cttatttac aataaaactt tgctgccacc tgtgtgtctg     2584
aggggtg                                                              2591
```

<210> SEQ ID NO 4
<211> LENGTH: 393
<212> TYPE: PRT
<213> ORGANISM: Homo sapiens

<400> SEQUENCE: 4

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110
```

-continued

```
Phe Leu His Ser Gly Thr Ala Lys Ser Val Thr Cys Thr Tyr Ser Pro
        115             120             125
Ala Leu Asn Lys Met Phe Cys Gln Leu Ala Lys Thr Cys Pro Val Gln
        130             135             140
Leu Trp Val Asp Ser Thr Pro Pro Gly Thr Arg Val Arg Ala Met
145             150             155             160
Ala Ile Tyr Lys Gln Ser Gln His Met Thr Glu Val Val Arg Arg Cys
                165             170             175
Pro His His Glu Arg Cys Ser Asp Ser Asp Gly Leu Ala Pro Pro Gln
            180             185             190
His Leu Ile Arg Val Glu Gly Asn Leu Arg Val Glu Tyr Leu Asp Asp
        195             200             205
Arg Asn Thr Phe Arg His Ser Val Val Val Pro Tyr Glu Pro Pro Glu
        210             215             220
Val Gly Ser Asp Cys Thr Thr Ile His Tyr Asn Tyr Met Cys Asn Ser
225             230             235             240
Ser Cys Met Gly Gly Met Asn Arg Arg Pro Ile Leu Thr Ile Ile Thr
                245             250             255
Leu Glu Asp Ser Ser Gly Asn Leu Leu Gly Arg Asn Ser Phe Glu Val
            260             265             270
Arg Val Cys Ala Cys Pro Gly Arg Asp Arg Arg Thr Glu Glu Glu Asn
        275             280             285
Leu Arg Lys Lys Gly Glu Pro His His Glu Leu Pro Pro Gly Ser Thr
    290             295             300
Lys Arg Ala Leu Pro Asn Asn Thr Ser Ser Ser Pro Gln Pro Lys Lys
305             310             315             320
Lys Pro Leu Asp Gly Glu Tyr Phe Thr Leu Gln Ile Arg Gly Arg Glu
                325             330             335
Arg Phe Glu Met Phe Arg Glu Leu Asn Glu Ala Leu Glu Leu Lys Asp
            340             345             350
Ala Gln Ala Gly Lys Glu Pro Gly Gly Ser Arg Ala His Ser Ser His
        355             360             365
Leu Lys Ser Lys Lys Gly Gln Ser Thr Ser Arg His Lys Lys Leu Met
    370             375             380
Phe Lys Thr Glu Gly Pro Asp Ser Asp
385             390
```

METHOD FOR TREATING CANCER BY COMBINED USE

This application claims the benefit under 35 U.S.C. § 111(a) as a continuation application of International Application No. PCT/JP2016/054822, filed Feb. 19, 2016, entitled "COMBINATION METHOD FOR TREATING CANCER," which claims priority to Japanese Patent Application No. 2015-032201, filed Feb. 20, 2015.

TECHNICAL FIELD

The present invention relates to a medicament and a method for treating cancer comprising a compound having murine double minute 2 (MDM2) inhibiting activity and a compound having Fms-like tyrosine kinase 3 (FLT3) inhibiting activity in combination.

BACKGROUND ART p53 is known as an important factor for inhibiting canceration of cells. p53 is a transcription factor that induces the expression of genes involved in the cell cycle and cellular apoptosis in response to various stresses. p53 is thought to inhibit canceration of cells by a transcription regulating function thereof. In fact, deletion or mutation of the p53 gene is observed in about half of human cancer cases.

Meanwhile, overexpression of murine double minute 2 (MDM2), a type of E3 ubiquitin ligase, is known as a factor for canceration of cells that are cancerated in spite of the presence of normal p53. MDM2 is a protein whose expression is induced by p53. MDM2 negatively regulates p53 by binding to the transcription activity domain of p53 to decrease the transcription activity of p53, exporting p53 out of the nucleus, and mediating degradation of p53 by acting as an ubiquitination ligase against p53. Therefore, it is thought that inactivation of functions of and degradation of p53 are promoted in cells in which MDM2 is overexpressed, resulting in canceration (Non Patent Document 1).

Paying attention to such functions of MDM2, many approaches have been attempted using substances that inhibit the suppression of p53 functions by MDM2 as candidate anti-tumor agents. Examples of MDM2 inhibitors targeting the MDM2-p53 binding site have been reported, which include spirooxindole derivatives (Patent Documents 1 to 15 and Non Patent Documents 1 to 3), indole derivatives (Patent Document 16), pyrrolidine-2-carboxamide derivatives (Patent Document 17), pyrrolidinone derivatives (Patent Document 18), isoindolinone derivatives (Patent Document 19 and Non Patent Document 4) and dispiropyrrolidine compounds (Patent Document 20).

FLT3 is a protein belonging to receptor tyrosine kinase class III together with KIT, FMS and PDGFR, etc., and is thought to be involved in the hematopoietic system (Non Patent Documents 5 to 8). Its structure has an extracellular region composed of five immunoglobulin-like domains, one juxtamembrane region (JM domain), two tyrosine kinase domains (TK1 and TK2) divided by a kinase insert domain (KI domain), and a C-terminal domain. FLT3 is highly expressed in brain, placenta, liver and hematopoietic stem cells (Non Patent Documents 6 to 9).

A ligand of FLT3 (FL) is expressed in stromal cells of bone marrow and stimulates stem cells, either alone or in collaboration with other cytokines (Non Patent Documents 10 to 13). The ligand-receptor interaction between FL and FLT3 is considered to have important functions in the hematopoietic system.

Meanwhile, high expression of FLT3 is observed in most cases in samples of acute myeloid leukemia (AML) or acute lymphatic leukemia (ALL) patients, and high expression of FLT3 is also seen in chronic myeloid leukemia (CML). It is also known that growth of AML cells is more remarkably enhanced than that of ALL cells by stimulation of FL (Non Patent Documents 14 to 18). The FLT3 gene is the gene that is most frequently mutated in acute myeloid leukemia (AML) cases, and either of internal tandem duplications (ITDs) in the juxtamembrane region (Non Patent Document 19) or a mutation in the FLT3 activation loop region (Non Patent Document 20) is confirmed in approximately 30% to 35% of patients. The mutation of FLT3-ITD or the activation loop region is associated with constitutive activation of tyrosine kinase activity.

N-(5-tert-Butyl-isoxazol-3-yl)-N'-{4-[7-(2-morpholin-4-yl-ethoxy)imidazo[2,1-b][1,3]benzothiazol-2-yl]phenyl}urea (quizartinib) having FLT3 inhibiting activity is known to have anti-tumor activity. Treatment of various cancers using quizartinib has been proposed in documents. Various dosing regimens have been reported. See, for example, Patent Documents 21 to 23 (which are incorporated herein by reference in their entirety). Also, the effects of combined use of quizartinib and anthracycline, a topoisomerase inhibitor or a tumor cell metabolic antagonist have been reported (Patent Document 24).

As for the relation between an MDM2 inhibitor and a FLT3 inhibitor, it has been reported that administration of an MDM2 inhibitor is preferred for patients whose cells contain FLT3 having an activating mutation (Patent Document 25). This document also states that combined administration of a FLT3 inhibitor and an MDM2 inhibitor is preferred for patients whose cells contain FLT3 having an activating mutation, but it does not disclose specific effects of the combined use of specific drugs.

There are various reports on the effects of combined use of various MDM2 inhibitors and various anti-tumor agents (Patent Documents 26 to 29).

CITATION LIST

Patent Documents

Patent Document 1: WO2006/091646
Patent Document 2: WO2006/136606
Patent Document 3: WO2007/104664
Patent Document 4: WO2007/104714
Patent Document 5: WO2008/034736
Patent Document 6: WO2008/036168
Patent Document 7: WO2008/055812
Patent Document 8: WO2008/141917
Patent Document 9: WO2008/141975
Patent Document 10: WO2009/077357
Patent Document 11: WO2009/080488
Patent Document 12: WO2010/084097
Patent Document 13: WO2010/091979
Patent Document 14: WO2010/094622
Patent Document 15: WO2010/121995
Patent Document 16: WO2008/119741
Patent Document 17: WO2010/031713
Patent Document 18: WO2010/028862
Patent Document 19: WO2006/024837
Patent Document 20: WO2012/121361
Patent Document 21: U.S. Patent Application Publication US 2007/0232604
Patent Document 22: U.S. Patent Application Publication US 2009/0123418

Patent Document 23: U.S. Patent Application Publication US 2009/0131426
Patent Document 24: WO2010/111172
Patent Document 25: WO2011/127058
Patent Document 26: EP1712235
Patent Document 27: WO2007/115289
Patent Document 28: WO2013/139724
Patent Document 29: WO2014/107713

Non Patent Documents

Non Patent Document 1: J. Am. Chem. Soc., 2005, 127, 10130-10131
Non Patent Document 2: J. Med. Chem., 2006, 49, 3432-3435
Non Patent Document 3: J. Med. Chem., 2009, 52, 7970-7973
Non Patent Document 4: J. Med. Chem., 2006, 49, 6209-6221
Non Patent Document 5: Genomics, 1991, 19, 380-385
Non Patent Document 6: Oncogene, 1991, 6, 1641-1650
Non Patent Document 7: Cell, 1991, 65, 1143-1152
Non Patent Document 8: Blood, 1993, 82, 1110-1119
Non Patent Document 9: Blood, 1996, 87, 1317-1325
Non Patent Document 10: Nature, 1994, 368, 643-648
Non Patent Document 11: Blood, 1995, 86, 3413-3420
Non Patent Document 12: Blood, 1995, 85, 1762-1768
Non Patent Document 13: Leukemia, 1996, 10, 1012-1018
Non Patent Document 14: Blood, 1995, 86, 4105-4114
Non Patent Document 15: Leukemia, 1996, 10, 1584-1591
Non Patent Document 16: Blood, 1996, 88, 3987-3997
Non Patent Document 17: Blood, 1992, 80, 2584-2593
Non Patent Document 18: Leukemia, 1996, 10, 261-270
Non Patent Document 19: Leukemia, 1996, 10, 1911-1918
Non Patent Document 20: Blood, 2001, 97 2434-2439

SUMMARY OF INVENTION

Technical Problem

An object of the present invention is to provide a medicament and a method for treating cancer comprising a compound having MDM2 inhibiting activity and a compound having FLT3 inhibiting activity in combination.

Solution to the Problem

As a result of extensive studies, the present inventors have found that use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide, which is a compound having MDM2 inhibiting activity, or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea, which is a compound having FLT3 inhibiting activity, or a pharmaceutically acceptable salt thereof in combination particularly produces an excellent anti-tumor effect while keeping adverse reaction (e.g. weight loss) low, and accomplished the present invention.

Specifically, the present invention relates to the following [1] to [21]:

[1] A medicament for cancer treatment comprising (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof which are administered in combination.

[2] A medicament according to claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof are separately contained as active ingredients in different formulations and administered at the same time or different times.

[3] A medicament according to claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof are contained in a single formulation.

[4] A medicament according to claim 1, wherein the medicament is a kit formulation comprising the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof.

[5] A method for treating cancer comprising administering (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof in combination.

[6] A medicament according to any one of claims 1 to 4, wherein the respective salts of the compounds are (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide p-toluenesulfonate and N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride.

[7] A treatment method according to claim 5, wherein the respective salts of the compounds are (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide p-toluenesulfonate and N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride.

[8] A medicament according to any one of claims 1 to 4 and 6, wherein the cancer is blood cancer (leukemia, lymphoma or multiple myeloma), brain tumor, head and neck cancer, esophageal cancer, stomach cancer, appendix cancer, colon cancer, anus cancer, gallbladder cancer, cholangiocarcinoma, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer or testicular cancer.

[9] A treatment method according to claim 5 or 7, wherein the cancer is blood cancer (leukemia, lymphoma or multiple myeloma), brain tumor, head and neck cancer, esophageal cancer, stomach cancer, appendix cancer, colon cancer, anus cancer, gallbladder cancer, cholangiocarcinoma cancer, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer or testicular cancer.

[10] A medicament according to any one of claims 1 to 4 and 6, wherein the cancer is leukemia.

[11] A treatment method according to claim 5 or 7, wherein the cancer is leukemia.

[12] A medicament according to any one of claims 1 to 4 and 6, wherein the cancer is leukemia having an activating mutation of FLT3.

[13] A treatment method according to claim 5 or 7, wherein the cancer is leukemia having an activating mutation of FLT3.

[14] A medicament according to any one of claims 1 to 4 and 6, wherein the cancer is acute myeloid leukemia (AML).

[15] A treatment method according to claim 5 or 7, wherein the cancer is acute myeloid leukemia (AML).

[16] A medicament according to any one of claims 1 to 4 and 6, wherein the cancer is acute myeloid leukemia (AML) having a FLT3-ITD mutation.

[17] A treatment method according to claim 5 or 7, wherein the cancer is acute myeloid leukemia (AML) having a FLT3-ITD mutation.

[18] A medicament according to any one of claims 1 to 4 and 6, wherein the cancer has wild-type TP53.

[19] A treatment method according to claim 5 or 7, wherein the cancer is cancer having wild-type TP53.

[20] A medicament according to any one of claims 1 to 4 and 6, wherein the cancer is cancer confirmed to be MDM2 inhibitor-sensitive using a gene signature.

[21] A treatment method according to claim 5 or 7, wherein the cancer is confirmed to be MDM2 inhibitor-sensitive using a gene signature.

Advantageous Effects of Invention

The present invention is useful as a method for treating cancer and/or an anti-cancer agent.

BRIEF DESCRIPTION OF DRAWINGS

FIG. 1-1 is a diagram showing in vivo effects of combined use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide tosylate (Compound A) and N-(5-tert-butyl-isoxazol-3-yl)-N'-{4-[7-(2-morpholin-4-yl-ethoxy)imidazo[2,1-b][1,3]benzothiazol-2-yl]phenyl}urea (quizartinib) on subcutaneously transplanted tumors of human acute myeloid leukemia cell line MOLM-13 having a FLT3-ITD mutation and wild-type TP53 in mice, and body weight change caused by combined administration thereof. The symbol x depicts an untreated control group, the symbol open circle depicts 0.5 mg/kg quizartinib, the symbol filled circle depicts 1 mg/kg quizartinib, the symbol open triangle depicts 25 mg/kg Compound A, the symbol open square depicts 25 mg/kg Compound A+0.5 mg/kg quizartinib, and the symbol filled square depicts 25 mg/kg Compound A+1 mg/kg quizartinib. The horizontal axis shows the number of days after tumor inoculation. The vertical axis of the upper panel shows estimated tumor volume calculated from tumor size. The vertical axis of the lower panel shows body weight change % relative to body weight on the first day of administration. The symbol filled triangle on the horizontal axis depicts the administration day of each compound. The error bar represents SE for the upper panel and SD for the lower panel.

FIG. 1-2 is a diagram showing in vivo effects of combined use of (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide tosylate (Compound A) and N-(5-tert-butyl-isoxazol-3-yl)-N'-{4-[7-(2-morpholin-4-yl-ethoxy)imidazo[2,1-b][1,3]benzothiazol-2-yl]phenyl}urea (quizartinib) on subcutaneously transplanted tumors of human acute myeloid leukemia cell line MOLM-13 having a FLT3-ITD mutation and wild-type TP53 in mice, and body weight change caused by combined administration thereof. The symbol x depicts an untreated control group, the symbol open circle depicts 0.5 mg/kg quizartinib, the symbol filled circle depicts 1 mg/kg quizartinib, the symbol filled triangle depicts 50 mg/kg Compound A, the symbol open square depicts 50 mg/kg Compound A+0.5 mg/kg quizartinib, and the symbol filled square depicts 50 mg/kg Compound A+1 mg/kg quizartinib. The abscissa shows the number of days after tumor inoculation. The ordinate of the upper panel shows estimated tumor volume calculated from tumor size. The ordinate of the lower panel shows body weight change % relative to body weight on the first day of administration. The symbol filled triangle on the abscissa depicts the administration day of each compound. The error bar represents SE for the upper panel and SD for the lower panel.

DESCRIPTION OF EMBODIMENTS

In the present invention, the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide is a compound of Example 70 in WO2012/121361. This compound can be produced by a method described in WO2012/121361 (WO2012/121361 is incorporated herein by reference in its entirety).

In the present invention, the N-(5-tert-butyl-isoxazol-3-yl)-N'-{4-[7-(2-morpholin-4-yl-ethoxy)imidazo[2,1-b][1,3]benzothiazol-2-yl]phenyl}urea is also referred to as 1-(5-tert-butyl-1,2-oxazol-3-yl)-3-(4-{7-[2-(morpholin-4-yl)ethoxy]imidazo[2,1-b][1,3]benzothiazol-2-yl}phenyl)urea or also referred to as quizartinib or AC220. This compound is represented by the following formula:

[Formula 1]

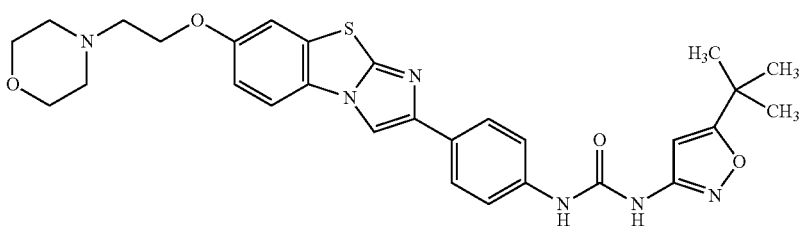

This compound can be produced by a method described in WO2007/109120 (WO2007/109120 is incorporated herein by reference in its entirety).

In the present invention, the (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and the N-(5-tert-butyl-isoxazol-3-yl)-N'-{4-[7-(2-morpholin-4-yl-ethoxy)imidazo[2,1-b][1,3]benzothiazol-2-yl]phenyl}urea may be various pharmaceutically acceptable salts.

Examples of the salts can include: hydrohalides such as hydrochloride and hydroiodide; inorganic acid salts such as nitrate, perchlorate, sulfate and phosphate; lower alkanesulfonates such as methanesulfonate, trifluoromethanesulfonate and ethanesulfonate; arylsulfonates such as benzenesulfonate and p-toluenesulfonate; organic acid salts such as formic acid, acetic acid, malic acid, fumarate, succinate, citrate, tartrate, oxalate and maleate; amino acid salts such as ornithine salt, glutamate and aspartate; alkali metal salts such as sodium salt, potassium salt and lithium salt; alkaline earth metal salts such as calcium salt and magnesium salt; inorganic salts such as ammonium salt; and organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'-dibenzylethylenediamine salt, diethanolamine salt, N-benzyl-N-(2-phenylethoxy)amine salt, piperazine salt, tetramethylammonium salt and tris(hydroxymethyl)aminomethane salt.

The salt of the (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide is preferably p-toluenesulfonate. The salt of the N-(5-tert-butyl-isoxazol-3-yl)-N'-{4-[7-(2-morpholin-4-yl-ethoxy)imidazo[2,1-b][1,3]benzothiazol-2-yl]phenyl}urea is preferably hydrochloride, particularly, dihydrochloride.

In the present invention, the (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and the N-(5-tert-butyl-isoxazol-3-yl)-N'-{4-[7-(2-morpholin-4-yl-ethoxy)imidazo[2,1-b][1,3]benzothiazol-2-yl]phenyl}urea or their pharmaceutically acceptable salts may each be present in a free or solvate form. The compound represented by general formula (1) of the present invention or the salt thereof may be present in a hydrate form, for example, by absorbing moisture in the air. The solvate is not particularly limited so long as it is pharmaceutically acceptable. Specifically, the solvate is preferably a hydrate, an ethanol solvate or the like. Moreover, the compound represented by general formula (1) may be in an N-oxide form when containing a nitrogen atom. These solvate and N-oxide forms are also included in the present invention.

The (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and the N-(5-tert-butyl-isoxazol-3-yl)-N'-{4-[7-(2-morpholin-4-yl-ethoxy)imidazo[2,1-b][1,3]benzothiazol-2-yl]phenyl}urea or their pharmaceutically acceptable salts may have stereoisomers depending on their structures. The compounds or the salts also encompass all these stereoisomers and mixtures of these stereoisomers in any ratio. The stereoisomers are as defined in 1996 IUPC, Pure and Applied Chemistry 68, 2193-2222. When the (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and the N-(5-tert-butyl-isoxazol-3-yl)-N'-{4-[7-(2-morpholin-4-yl-ethoxy)imidazo[2,1-b][1,3]benzothiazol-2-yl]phenyl}urea or their pharmaceutically acceptable salts are each present as tautomers, these tautomers may be present in equilibrium or a certain form may be dominantly present. All these cases are included in the scope of the present invention. The tautomers refer to isomers resulting from the shift of a proton of one atom of the molecule to another atom.

The (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide and the N-(5-tert-butyl-isoxazol-3-yl)-N'-{4-[7-(2-morpholin-4-yl-ethoxy)imidazo[2,1-b][1,3]benzothiazol-2-yl]phenyl}urea or their pharmaceutically acceptable salts may each be a "pharmaceutically acceptable prodrug compound" that is converted to the desired compound through enzymatic oxidation, reduction, hydrolysis or the like or through hydrolysis or the like induced by gastric acid or the like, due to a reaction induced by an enzyme, gastric acid or the like under physiological conditions in vivo.

Examples of the prodrug include compounds obtained by acylation, alkylation or phosphorylation.

Prodrugs of the compounds can be produced from the compound (1) according to a method known in the art. Moreover, prodrugs of the compounds also include those converted to the desired compounds under physiological conditions as described in "Development of Pharmaceutical Products", vol. 7, Molecule Design, p. 163-198, Hirokawa-Shoten Ltd. (1990).

In the present invention, the terms "tumor" and "cancer" are used interchangeably. Furthermore, in the present invention, tumor, malignant tumor, cancer, malignant neoplasm, carcinoma, sarcoma, and the like may be collectively referred to as "tumor" or "cancer".

In the present invention, "FLT3" means Fms-like tyrosine kinase 3 (FLT3) and has the same meaning as FLK2, STK1, CD135 and FLK-2. FLT3 also includes homologs derived from various animal species. Human FLT3 is a molecule registered in NCBI under RefSEQ: accession NM_004119.2 (protein: RefSeq NP_004110.2).

FLT3 mRNA has a sequence as given below. However, it should be understood that even FLT3 having no mutation may differ in sequence among individuals due to polymorphism, etc.

acctgcagcgcgaggcgcgccgctccaggcggcatcgcagggctgggcc
ggcgcggcctggggaccccgggctccggaggccatgccggcgttggcgc
gcgacggcggccagctgccgctgctcgttgttttttctgcaatgatatt
tgggactattacaaatcaagatctgcctgtgatcaagtgtgttttaatc
aatcataagaacaatgattcatcagtggggaagtcatcatcatatccca
tggtatcagaatccccggaagacctcgggtgtgcgttgagaccccagag
ctcagggacagtgtacgaagctgccgctgtggaagtggatgtatctgct
tccatcacactgcaagtgctggtcgacgcccagggaacatttcctgtc
tctgggtctttaagcacagctccctgaattgccagccacattttgattt
acaaaacagaggagttgtttccatggtcattttgaaaatgacagaaacc
caagctggagaatacctacttttttattcagagtgaagctaccaattaca
caatattgtttacagtgagtataagaaatacctgctttacacattaag
aagaccttacttttgaaaaaatggaaaaccaggacgccctggtctgcata
tctgagagcgttccagagccgatcgtggaatgggtgctttgcgattcac
aggggggaaagctgtaaagaagaaagtccagctgttgttaaaaaggagga
aaaagtgcttcatgaattatttgggacggacataaggtgctgtgccaga
aatgaactgggcagggaatgcaccaggctgttcacaatagatctaaatc
aaactcctcagaccacattgccacaattatttcttaaagtaggggaacc
cttatggataaggtgcaaagctgttcatgtgaaccatggattcgggctc
acctgggaattagaaaacaaagcactcgaggagggcaactactttgaga
tgagtacctattcaacaaacagaactatgatacggattctgtttgcttt
tgtatcatcagtggcaaagaacgacaccggatactacacttgttcctct
tcaaagcatcccagtcaatcagctttggttaccatcgtagaaaagggat
ttataaatgctaccaattcaagtgaagattatgaaattgaccaatatga
agagttttgttttctgtcaggtttaaagcctacccacaaatcagatgt
acgtggaccttctctcgaaaatcatttccttgtgagcaaaagggtcttg
ataacggatacagcatatccaagttttgcaatcataagcaccagccagg
agaatatatattccatgcagaaaatgatgatgcccaatttaccaaaatg
ttcacgctgaatataagaaggaaacctcaagtgctcgcagaagcatcgg
caagtcaggcgtcctgtttctcggatggatacccattaccatcttggac
ctggaagaagtgttcagacaagtctcccaactgcacagaagagatcaca
gaaggagtctgaatagaaaggctaacagaaaagtgtttggacagtggg
tgtcgagcagtactctaaacatgagtgaagccataaaagggttcctggt caagtgctgtgcatacaattcccttggcacatcttgtgagacgatcctt
ttaaactctccaggcccctttcccttctatccaagacaacatctcattct
atgcaacaattggtgtttgtctcctcttcattgtcgttttaaccctgct
aatttgtcacaagtacaaaaagcaatttaggtatgaaagccagctacag
atggtacaggtgaccggctcctcagataatgagtacttctacgttgatt
tcagagaatatgaatatgatctcaaatgggagtttccaagagaaaattt
agagtttgggaaggtactaggatcaggtgcttttggaaaagtgatgaac
gcaacagcttatggaattagcaaaacaggagtctcaatccaggttgccg
tcaaaatgctgaaagaaaaagcagacagctctgaaagagaggcactcat
gtcagaactcaagatgatgacccagctgggaagccacgagaatattgtg
aacctgctggggcgtgcacactgtcaggaccaatttacttgattttttg
aatactgttgctatggtgatcttctcaactatctaagaagtaaaagaga
aaaatttcacaggacttggacagagattttcaaggaacacaatttcagt
ttttaccccactttccaatcacatccaaattccagcatgcctggttcaa
gagaagttcagatacacccggactcggatcaaatctcagggcttcatgg
gaattcatttcactctgaagatgaaattgaatatgaaaaccaaaaaagg
ctggaagaagaggaggacttgaatgtgcttacatttgaagatcttcttt
gctttgcatatcaagttgccaaaggaatggaatttctggaatttaagtc
gtgtgttcacagagacctggccgccaggaacgtgcttgtcacccacggg
aaagtggtgaagatatgtgactttggattggctcgagatatcatgagtg
attccaactatgttgtcaggggcaatgcccgtctgcctgtaaaatggat
ggcccccgaaagcctgttgaaggcatctacaccattaagagtgatgtc
tggtcatatggaatattactgtgggaaatcttctcacttggtgtgaatc
cttaccctggcattccggttgatgctaacttctacaaactgattcaaaa
tggatttaaaatggatcagccatttttatgctacagaagaaatatacatt
ataatgcaatcctgctgggcttttgactcaaggaaacggccatccttcc
ctaatttgacttcgttttaggatgtcagctggcagatgcagaagaagc
gatgtatcagaatgtggatggccgtgtttcggaatgtcctcacacctac
caaaacaggcgacctttcagcagagagatggatttggggctactctctc
cgcaggctcaggtcgaagattcgtagaggaacaatttagttttaaggac
ttcatccctccacctatccctaacaggctgtagattaccaaaacaagat
taatttcatcactaaaagaaaatctattatcaactgctgcttcaccaga
cttttctctagaagctgtctgcgtttactcttgttttcaaagggacttt
tgtaaaatcaaatcatcctgtcacaaggcaggaggagctgataatgaac
tttattggagcattgatctgcatccaaggccttctcaggctggcttgag
tgaattgtgtacctgaagtacagtatattcttgtaaatacataaaacaa
aagcattttgctaaggagaagctaatatgatttttttaagtctatgttt
aaaataatatgtaaattttttcagctatttagtgatatattttatgggtg
ggaataaaattttctactacagaattgcccattattgaattatttacatg
gtataattagggcaagtcttaactggagttcacgaacccctgaaattg -continued
```
tgcacccatagccacctacacattccttccagagcacgtgtgcttttac cccaagatacaaggaatgtgtaggcagctatggttgtcacagcctaaga tttctgcaacaacaggggttgtattgggggaagtttataatgaataggt gttctaccataaagagtaatacatcacctagacactttggcggccttcc cagactcagggccagtcagaagtaacatggaggattagtattttcaata aagttactcttgtccccacaaaaaaa.
```

FLT3 protein has an amino acid sequence as described below. However, it should be understood that even FLT3 having no mutation may differ in sequence among individuals due to polymorphism, etc.

```
mpalardggqlpllvvfsamifgtitnqdlpvikcvlinhknndssvgk sssypmvsespedlgcalrpgssgtvyeaaavevdvsasitlqvlvdap gnisclwvfkhsslncqphfdlqnrgvvsmvilkmtetgageyllfigs eatnytilftvsirntllytlrrpyfrkmengdalvcisesvpepivew vlcdsggesckeespavvkkeekvlhelfgtdirccarnelgrectrlf tidlnqtpqttlpqlflkvgeplwirckavhvnhgfgltwelenkalee gnyfemstystnrtmirilfafvssvarndtgyytcssskhpsqsalvt ivekgfinatnssedyeidgyeefcfsvrfkaypgirctwtfsrksfpc eqkgldngysiskfcnhkhqpgeyifhaenddagftkmftlnirrkpqv laeasasgascfsdgyplpswtwkkcsdkspncteeitegvwnrkanrk vfgqwvssstlnmseaikgflvkccaynslgtscetillnspgpfpfiq dnisfyatigvcllfivvltllichkykkgfryesqlqmvqvtgssdne yfyvdfreyeydlkwefprenlefgkvlgsgafgkvmnataygisktgv siqvavkmlkekadsserealmselkmmtqlgshenivnllgactlsgp iylifeyccygdllnylrskrekfhrtwteifkehnfsfyptfqshpns smpgsrevgihpdsdgisglhgnsfhsedeieyengkrleeeedlnvlt fedllcfayqvakgmeflefkscvhrdlaarnvlvthgkvvkicdfgla rdimsdsnyvvrgnarlpvkwmapeslfegiytiksdvwsygillweif slgvnpypgipvdanfykligngfkmdgpfyateeiyiimqscwafdsr krpsfpnitsflgcgladaeeamyqnvdgrvsecphtygnrrpfsremd lgllspqaqvedS.
```

In the present invention, "activating mutation of FLT3" means a mutation that causes ligand-independent activation of FLT3. Examples thereof include, but are not particularly limited to, internal tandem duplications (ITDs) in the juxtamembrane region (JM region), and point mutations D835V, D835E, D835N, D835Y and D835H that occur in the activation loop region of FLT3. The FLT3-ITD mutation occurs mainly in exon 14 of the JM region and is also found in exon 15.

In the present invention, "wild-type TP53" means that a gene TP53 encoding p53 protein is a gene having a sequence registered in NCBI under RefSEQ: accession NM_000546 (protein: RefSeq NP_000537).

Wild-type TP53 mRNA has a sequence given below. However, it should be understood that even TP53 having no mutation may differ in sequence among individuals due to polymorphism, etc.

```
gatgggattggggttttcccctcccatgtgctcaagactggcgctaaaag ttttgagcttctcaaaagtctagagccaccgtccagggagcaggtagctg ctgggctccggggacactttgcgttcgggctgggagcgtgctttccacga cggtgacacgcttccctggattggcagccagactgccttccgggtcactg ccatggaggagccgcagtcagatcctagcgtcgagcccctctgagtcag gaaacattttcagacctatggaaactacttcctgaaaacaacgttctgtc cccttgccgtcccaagcaatggatgatttgatgctgtcccggacgata ttgaacaatggttcactgaagacccaggtccagatgaagctcccagaatg ccagaggctgctccccgtggccctgcaccagcagctcctacaccggc ggccctgcaccagcccctcctggccctgtcatcttctgtcccttccc agaaaacctaccagggcagctacggtttccgtctgggcttcttgcattct gggacagccaagtctgtgacttgcacgtactccctgccctcaacaagat gttttgccaactggccaagacctgccctgtgcagctgtgggttgattcca cacccccgcccggcacccgcgtccgcgccatggccatctacaagcagtca cagcacatgacggaggttgtgaggcgctgccccaccatgagcgctgctc agatagcgatggtctggcccctcctcagcatcttatccgagtggaaggaa atttgcgtgtggagtatttggatgacagaaacacttttcgacatagtgtg gtggtgccctatgagccgcctgaggttggctctgactgtaccaccatcca ctacaactacatgtgtaacagttcctgcatgggcggcatgaaccggaggc ccatcctcaccatcatcacactggaagactccagtggtaatctactggga cggaacagctttgaggtgcgtgtttgtgcctgtcctgggagagaccggcg cacagaggaagagaatctccgcaagaaaggggagcctcaccacgagctgc ccccagggagcactaagcgagcactgcccaacaacaccagctcctctccc cagccaaagaagaaaccactggatggagaatatttcacccttcagatccg tgggcgtgagcgcttcgagatgttccgagagctgaatgaggccttggaac tcaaggatgcccaggctgggaaggagccaggggggagcgggctcactcca gccacctgaagtccaaaaagggtcagtctacctcccgccataaaaaactc atgttcaagacagaagggcctgactcagactgacattctccacttcttgt tccccactgacagcctcccacccccatctctccctcccctgccattttgg gttttgggtctttgaaccctgcttgcaataggtgtgcgtcagaagcacc caggacttccatttgctttgtcccggggctccactgaacaagttggcctg cactggtgttttgttgtggggaggaggatggggagtaggacataccagct tagattttaaggtttttactgtgagggatgtttgggagatgtaagaaatg ttcttgcagttaagggttagtttacaatcagccacattctaggtaggggc ccacttcaccgtactaaccagggaagctgtccctcactgttgaattttct ctaacttcaaggcccatatctgtgaaatgctggcatttgcacctacctca cagagtgcattgtgagggttaatgaaataatgtacatctggccttgaaac ccctttattacatggggtctagaacttgacccccttgagggtgcttgt tccctctccctgttggtcggtgggttggtagtttctacagttgggcagct ggttaggtagagggagttgtcaagtctctgctggcccagccaaaccctgt ctgacaacctcttggtgaaccttagtacctaaaaggaaatctcacccat
```

-continued

```
cccacaccctggaggatttcatctcttgtatatgatgatctggatccacc aagacttgttttatgctcagggtcaatttcttttttcttttttttttttt ttttctttttctttgagactgggtctcgctttgttgcccaggctggagt ggagtggcgtgatcttggcttactgcagcctttgcctcccggctcgagc agtcctgcctcagcctccggagtagctgggaccacaggttcatgccacca tggccagccaacttttgcatgttttgtagagatggggtctcacagtgttg cccaggctggtctcaaactcctgggctcaggcgatccacctgtctcagcc tcccagagtgctgggattacaattgtgagccaccacgtccagctggaagg gtcaacatcttttacattctgcaagcacatctgcattttcaccccaccct tccccctccttctcccttttttatatcccatttttatatcgatctcttattt tacaataaaactttgctgccacctgtgtgtctgaggggtg.
```

TP53 protein has an amino acid sequence as described below. However, it should be understood that even TP53 having no mutation may differ in sequence among individuals due to polymorphism, etc.

```
meepgsdpsvepplsgetfsdlwkllpennvlsplpsgamddlmlspddi egwftedpgpdeaprmpeaappvapapaaptpaapapapswplsssvpsg ktyggsygfrlgflhsgtaksvtctyspalnkmfcglaktcpvglwvdst pppgtrvramaiykgsghmtevvrrophhercsdsdglappghlirvegn lrveylddrntfrhsvvvpyeppevgsdcttihynymcnsscmggmnrrp iltiitledssgnllgrnsfevrvcacpgrdrrteeenlrkkgephhelp pgstkralpnntssspgpkkkpldgeyftlgirgrerfemfrelnealel kdagagkepggsrahsshlkskkggstsrhkklmfktegpdsd.
```

In the present invention, "gene signature" means a single gene or a gene group consisting of a plurality of genes, a plurality of genes whose expression pattern is characteristic of a biological phenotype or a medical condition, such as morbidity of a certain disease, response to a certain medicament, or prognosis of a certain disease.

In the present invention, "biological sample" refers to tissues, liquids or cells isolated from an individual, or a mixture thereof. Examples thereof can include, but are not limited to, tumor biopsy, spinal fluid, pleural fluid, intra-abdominal fluid, lymph, skin sections, blood, urine, feces, sputum, respiratory organ, intestinal tract, genitourinary tract, saliva, milk, digestive organ, and cells collected therefrom. Preferred examples of a "biological sample" can include a portion of test subject-derived resected tissues obtained during surgery performed for the purpose of treating a cancer disease, a portion of tissues collected by biopsy or the like from a test subject suspected of having a cancer disease, and cells derived from pleural fluid or intra-abdominal fluid.

The biological sample may be protein extracts or nucleic acid extracts prepared from tissues, liquids or cells isolated from an individual, or a mixture thereof, etc. The protein extracts or the nucleic acid extracts can be prepared by use of a protein preparation method or a nucleic acid preparation method known per se in the art.

One aspect of the present invention relates to a medicament for cancer treatment comprising (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof which are administered in combination.

In the present invention, a "medicament" comprising (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof "which are administered in combination" is a medicament based on the assumption that both the drugs are administered in combination.

In the present invention, the "administration in combination" of (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof means that both the drugs are incorporated into the body of a recipient in a given period. A formulation containing both the drugs in a single formulation may be administered, or the drugs may be prepared into separate formulations and separately administered. In the case of preparing separate formulations, the timing of their administration is not particularly limited. The separate formulations may be administered at the same time or may be administered at different times or on different days in a staggered manner. In the case of administering the (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof at different times or on different days, the order of their administration is not particularly limited. Usually, these formulations are administered according to their respective administration methods. Therefore, these formulations may be administered in the same number of doses or may be administered in a different number of doses. Also, in the case of preparing separate formulations, the respective administration methods (administration routes) of the formulations may be the same as each other, or these formulations may be administered by different administration methods (administration routes). Both the drugs do not have to exist at the same time in the body and may be incorporated into the body over a given period (e.g., 1 month, preferably 1 week, more preferably a few days, even more preferably 1 day). One of the active ingredients may have disappeared from the body at the time of administration of the other active ingredient.

Examples of a dosage form of the medicament of the present invention include 1) administration of a single formulation comprising (3'R,4'S,5'R)—N-[(3R,6S)-6-carbamoyltetrahydro-2H-pyran-3-yl]-6''-chloro-4'-(2-chloro-3-fluoropyridin-4-yl)-4,4-dimethyl-2''-oxo-1'',2''-dihydrodispiro[cyclohexane-1,2'-pyrrolidine-3',3''-indole]-5'- carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, 2) concurrent administration through the same administration route of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, 3) administration in a staggered manner through the same administration route of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, 4) concurrent administration through different administration routes of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, and 5) administration in a staggered manner through different administration routes of two formulations separately prepared from (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof.

In the present invention, the two different formulations may be in the form of a kit comprising these formulations.

A medicament according to the present invention can contain (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and/or N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof and a pharmaceutically acceptable carrier and can be administered as various injections such as intravenous injection, intramuscular injection, and subcutaneous injection or by various methods such as oral administration or percutaneous administration. A pharmaceutically acceptable carrier means a pharmaceutically acceptable material that is involved in transport of the compound of the present invention or a composition containing the compound of the present invention (e.g., an excipient, a diluent, an additive and a solvent) from a given organ to another organ.

A formulation can be prepared by selecting a suitable formulation form (e.g., oral formulation or injection) depending on the administration method and using various methods conventionally used for preparing a formulation. Examples of oral formulations can include tablets, powders, granules, capsules, pills, lozenges, solutions, syrups, elixirs, emulsions and oily or aqueous suspensions. In oral administration, the free compound or a salt form may be used. An aqueous formulation can be prepared by forming an acid adduct with a pharmaceutically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization or the like. Furthermore, one dose may be filled in one vessel, or two or more doses may be filled in a vessel.

Examples of solid formulations include tablets, powders, granules, capsules, pills and lozenges. These solid formulations may contain pharmaceutically acceptable additives together with a compound of the present invention. Examples of additives include fillers, extenders, binders, disintegrating agents, dissolution promoting agents, skin wetting agents and lubricants. These additives can be selected and mixed as required to prepare a formulation.

Examples of liquid formulations include solutions, syrups, elixirs, emulsions and suspensions. Examples of additives include suspending agents and emulsifiers. These additives can be selected and mixed as required to prepare a formulation.

Examples of pharmaceutical materials can include, but are not limited to: amino acids such as glycine, alanine, glutamine, asparagine, arginine and lysine; antimicrobial agents; antioxidants such as ascorbic acid, sodium sulfate and sodium bisulfite; buffers such as phosphate, citrate or borate buffers, sodium bicarbonate and Tris-HCl solutions; fillers such as mannitol and glycine; chelating agents such as ethylenediaminetetraacetic acid (EDTA); complexing agents such as caffeine, polyvinylpyrrolidine, β-cyclodextrin and hydroxypropyl-β-cyclodextrin; bulking agents such as glucose, mannose and dextrin; other carbohydrates such as monosaccharides and disaccharides; coloring agents; corrigents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid and hydrogen peroxide; solvents such as glycerin, propylene glycol and polyethylene glycol; sugar alcohols such as mannitol and sorbitol; suspending agents; surfactants such as sorbitan ester, polysorbates such as polysorbate 20 and polysorbate 80, triton, tromethamine, lecithin and cholesterol; stability enhancers such as sucrose and sorbitol; elasticity enhancers such as sodium chloride, potassium chloride, mannitol and sorbitol; transport agents; excipients; and/or pharmaceutical additives. The amount of these pharmaceutical materials added is preferably 0.01 to 100 times, particularly, 0.1 to 10 times the weight of the drug. The recipe of a preferred pharmaceutical composition in a formulation can be appropriately determined by those skilled in the art according to an applicable disease, an applicable administration route, etc.

An excipient or a carrier in a pharmaceutical composition may be liquid or solid. Appropriate excipients or carriers may be other materials usually used in injectable water, physiological saline, artificial cerebrospinal fluid, and parenteral administration. Neutral physiological saline or physiological saline containing serum albumin may be used as a carrier. The pharmaceutical composition can contain a Tris buffer of pH 7.0 to 8.5, an acetate buffer of pH 4.0 to 5.5, or a citrate buffer of pH 3.0 to 6.2. These buffers can also contain sorbitol or other compounds.

Preferred examples of the formulation of the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof include formulations described in WO2014/055397 (WO2014/055397 is incorporated herein by reference in its entirety).

The medicament of the present invention can be used in cancer treatment of mammals, particularly, humans. The dose and the administration interval of the medicament of the present invention can be suitably selected depending on the site of the disease, the patient's height, body weight, sex, or medical history, according to a physician's discretion. When the medicament of the present invention is administered to a human, the dose range is approximately 0.01 to 500 mg/kg body weight, preferably, approximately 0.1 to 100 mg/kg body weight, per day with respect to one type of active ingredient. Preferably, the active ingredient of the present invention is administered to a human once a day, or the dose is divided two to four times, and administration is repeated at an appropriate interval. Furthermore, the daily dose may exceed the above-mentioned dose at a physician's discretion, if necessary.

For examples of the administration method of the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof, see a method described in WO2009/061446, a method described in WO2010/132787 and a method described in U.S. Pat. No. 8,357,690, all of which are incorporated herein by reference in their entirety. This active ingredient may be administered once a day for 1 week, 2 weeks, 3 weeks, 4 weeks or 5 weeks. Preferred examples thereof include a method of continuously administering 12 to 450 mg, for example, 20 mg, 30 mg, 40 mg, 50 mg, 60 mg, 90 mg, 135 mg, 200 mg, 300 mg or 450 mg, of this agent for 28 days, a method of continuously administering the above-mentioned dose for 8 to 21 days together with an additional anticancer agent, and a method of continuously administering the above-mentioned dose for 4 to 17 days together with an additional anticancer agent.

The type of cancer to be treated is not particularly limited as long as the cancer is confirmed to be sensitive to treatment by combined use of the present invention. Examples thereof include blood cancer (leukemia, lymphoma or multiple myeloma), brain tumor, head and neck cancer, esophageal cancer, stomach cancer, appendix cancer, colon cancer, anus cancer, gallbladder cancer, cholangiocarcinoma cancer, pancreatic cancer, gastrointestinal stromal tumor, lung cancer, liver cancer, mesothelioma, thyroid cancer, renal cancer, prostate cancer, neuroendocrine tumor, melanoma, breast cancer, endometrial cancer, cervical cancer, ovarian cancer, osteosarcoma, soft tissue sarcoma, Kaposi's sarcoma, myosarcoma, renal cancer, bladder cancer and testicular cancer. Among them, leukemia, particularly, acute myeloid leukemia (AML) is preferred. Leukemia having an activating mutation of FLT3 is more preferred, and acute myeloid leukemia having a FLT3-ITD mutation is particularly preferred.

In the present invention, a method for detecting the "activating mutation of FLT3" includes a method of detecting a mutation on genomic DNA as well as, when the mutation on the genomic DNA is reflected to base change in a transcription product or amino acid change in a translation product, a method of detecting this change in the transcription product or translation product (i.e., indirect detection), and a method based on detection of phosphorylated FLT3 because activation of FLT3 involves a rise in phosphorylation level.

In a preferred embodiment, a method for detecting a mutation includes a method of directly determining the nucleotide sequence of a gene region in a test subject-derived biological sample to thereby detect a mutation. In the present invention, the "FLT3 gene region" means a given region on genomic DNA containing the FLT3 gene. The region also contains the expression control regions (e.g., a promoter region and an enhancer region) of the FLT3 gene, the 3'-terminal untranslated region of the FLT3 gene, and the like. A mutation in these regions can influence, for example, the transcription activity of the FLT3 gene.

In this method, first, a DNA sample is prepared from a test subject-derived biological sample. Examples of the DNA sample include a genomic DNA sample and a cDNA sample prepared from RNA by reverse transcription.

The method for extracting genomic DNA or RNA from the biological sample is not particularly limited, and an approach known in the art can be appropriately selected for use. Examples of the method for extracting genomic DNA include a SDS phenol method (method which involves denaturing proteins in tissues preserved in a urea-containing solution or ethanol, using a proteolytic enzyme (proteinase K), a surfactant (SDS) and phenol, and extracting DNA by precipitation from the tissues using ethanol), and DNA extraction methods using Clean Columns® (manufactured by Nexttec Biotechnologie GmbH), AquaPure® (manufactured by Bio-Rad Laboratories, Inc.), ZR Plant/Seed DNA Kit (manufactured by Zymo Research Corp.), Aqua Genomic Solution® (manufactured by MoBiTec GmbH), prepGEM® (manufactured by ZyGEM NZ Ltd.) or BuccalQuick® (manufactured by TrimGen Corp.). Examples of the method for extracting RNA include extraction methods using phenol and a chaotropic salt (more specifically, extraction methods using a commercially available kit such as TRIzol (manufactured by Invitrogen Corp.) or ISOGEN (manufactured by Wako Pure Chemical Industries, Ltd.)), and methods using other commercially available kits (RNAPrep Total RNA Extraction Kit (manufactured by Beckman Coulter, Inc.), RNeasy Mini (manufactured by Qiagen N.V.), RNA Extraction Kit (manufactured by Pharmacia Biotech Inc.), etc.). Examples of reverse transcriptase for use in the preparation of cDNA from the extracted RNA include, but are not particularly limited to, reverse transcriptase derived from retrovirus such as RAV (Rous associated virus) or AMV (avian myeloblastosis virus), and reverse transcriptase derived from mouse retrovirus such as MMLV (Moloney murine leukemia virus).

In this embodiment, DNA containing a mutation site in the FLT3 gene region is subsequently isolated, and the nucleotide sequence of the isolated DNA is determined. The isolation of the DNA can be performed by, for example, PCR using a pair of oligonucleotide primers designed to flank the mutation in the FLT3 gene region, and the genomic DNA or the RNA as a template. The determination of the nucleotide sequence of the isolated DNA can be performed by a method generally known to those skilled in the art, such as the Maxam-Gilbert method or Sanger method.

The determined nucleotide sequence of the DNA or the cDNA can be compared with a control (e.g., the nucleotide sequence of DNA or cDNA derived from non-cancer tissues of the same test subject) to thereby determine the presence or absence of the mutation in the FLT3 gene region in the cancer cells of the test subject.

The method for detecting a mutation in the FLT3 gene region can be performed by various methods capable of detecting a mutation, in addition to the method of directly determining the nucleotide sequence of DNA or cDNA.

For example, in one of the methods, a DNA or cDNA sample is first prepared from the biological sample. Subsequently, a reporter fluorescent dye- and quencher fluorescent dye-labeled oligonucleotide probe having a nucleotide sequence complementary to a nucleotide sequence containing the mutation in the FLT3 gene region is prepared. Then, the oligonucleotide probe is hybridized to the DNA sample. Then, the nucleotide sequence containing the mutation in the FLT3 gene region is amplified using the DNA sample hybridized with the oligonucleotide probe as a template. Then, fluorescence emitted by the reporter fluorescent dye through the decomposition of the oligonucleotide probe associated with the amplification is detected. Subsequently, the detected fluorescence is compared with a control. Examples of such a method include a double die probe method, so-called TaqMan® probe method.

In an alternative method, a DNA or cDNA sample is prepared from the biological sample. Subsequently, the nucleotide sequence containing the mutation in the FLT3 gene region is amplified using the DNA sample as a template in a reaction system containing an intercalator that emits fluorescence upon insertion between two strands of DNA. Then, the temperature of the reaction system is changed, and variation in the intensity of the fluorescence emitted by the intercalator is detected. The detected variation in the intensity of the fluorescence caused by the change in the temperature is compared with a control. Examples of such a method include a high resolution melting (HRM) method.

In a further alternative method, a DNA or cDNA sample is first prepared from the biological sample. Subsequently, DNA containing a mutation site in the FLT3 gene region is amplified. Then, the amplified DNA is cleaved with restriction enzymes. Subsequently, the DNA fragments are separated according to their sizes. Subsequently, the detected sizes of the DNA fragments are compared with a control. Examples of such a method include a method using restriction fragment length polymorphism (RFLP) and PCR-RFLP.

In a further alternative method, a DNA or cDNA sample is first prepared from the biological sample. Subsequently, DNA containing a mutation site in the FLT3 gene region is amplified. Then, the amplified DNA is dissociated into single-stranded DNA. Subsequently, the single-stranded DNA thus obtained by dissociation is separated on a non-denaturing gel. The mobility of the separated single-stranded DNA on the gel is compared with a control. Examples of such a method include PCR-SSCP (single-strand conformation polymorphism).

In a further alternative method, a DNA or cDNA sample is first prepared from the biological sample. Subsequently, DNA containing a mutation site in the FLT3 gene region is amplified. Then, the amplified DNA is separated on a gel in which the concentration of a DNA denaturant is gradually elevated. Subsequently, the mobility of the separated DNA on the gel is compared with a control. Examples of such a method include denaturant gradient gel electrophoresis (DGGE).

A further alternative method is a method using DNA containing a mutation site in the FLT3 gene region prepared from the biological sample, and a substrate with immobilized oligonucleotide probes hybridizing to the DNA. Examples of such a method include a DNA array method.

In a further alternative method, a DNA or cDNA sample is first prepared from the biological sample. Also, an "oligonucleotide primer having a nucleotide sequence complementary to the base downstream by one base from the base at the mutation site in the FLT3 gene region, and a downstream nucleotide sequence thereof" is prepared. Subsequently, a ddNTP primer extension reaction is performed using the DNA as a template and the primer. Subsequently, the primer extension reaction product is applied to a mass spectrometer to conduct mass spectrometry. Subsequently, the genotype is determined from the mass spectrometry results. Then, the determined genotype is compared with a control. Examples of such a method include MALDI-TOF/MS.

In a further alternative method, a DNA or cDNA sample is first prepared from the biological sample. Subsequently, an oligonucleotide probe consisting of 5'—"a nucleotide sequence complementary to the base at the mutation site in the FLT3 gene region, and an upstream nucleotide sequence thereof"—"a nucleotide sequence hybridizing neither to the base downstream by one base from the mutation site in the FLT3 gene region, nor to a downstream nucleotide sequence thereof"—3' (flap) is prepared. Also, an "oligonucleotide probe having a nucleotide sequence complementary to the base at the mutation site in the FLT3 gene region, and a downstream nucleotide sequence thereof" is prepared. Subsequently, the prepared DNA is hybridized to these two types of oligonucleotide probes. Subsequently, the hybridized DNA is cleaved with a single-stranded DNA-cleaving enzyme to release the flap. Examples of the single-stranded DNA-cleaving enzyme include, but are not particularly limited to, cleavase. In this method, a fluorescent reporter- and fluorescent quencher-labeled oligonucleotide probe having a sequence complementary to the flap is then hybridized to the flap. Subsequently, the intensity of the generated fluorescence is measured. Then, the measured intensity of the fluorescence is compared with a control. Examples of such a method include an invader method.

In a further alternative method, a DNA or cDNA sample is first prepared from the biological sample. Subsequently, DNA containing a mutation site in the FLT3 gene region is amplified. Then, the amplified DNA is dissociated into single strands, and only one of the single strands of the dissociated DNA is separated. Subsequently, an extension reaction is performed one by one from a base close to the base at the mutation site in the FLT3 gene region. Pyrophosphoric acid generated during this reaction is enzymatically allowed to develop light. The intensity of the light is measured. The measured intensity of the fluorescence is compared with a control. Examples of such a method include pyrosequencing.

In a further alternative method, a DNA or cDNA sample is first prepared from the biological sample. Subsequently, DNA containing a mutation site in the FLT3 gene region is amplified. Subsequently, an "oligonucleotide primer having a nucleotide sequence complementary to the base downstream by one base from the base at the mutation site in the FLT3 gene region, and a downstream nucleotide sequence thereof" is prepared. Subsequently, a single-base extension reaction is performed using the amplified DNA as a template and the prepared primer in the presence of fluorescently labeled nucleotides. Then, the degree of polarization of fluorescence is measured. Subsequently, the measured degree of polarization of fluorescence is compared with a control. Examples of such a method include the AcycloPrime method.

In a further alternative method, a DNA or cDNA sample is first prepared from the biological sample. Subsequently, DNA containing a mutation site in the FLT3 gene region is amplified. Subsequently, an "oligonucleotide primer having a nucleotide sequence complementary to the base downstream by one base from the base at the mutation site in the FLT3 gene region, and a downstream nucleotide sequence thereof" is prepared. Subsequently, a single-base extension reaction is performed using the amplified DNA as a template and the prepared primer in the presence of fluorescently labeled nucleotides. Subsequently, the base species used in the single-base extension reaction are determined. Then, the determined base species are compared with a control. Examples of such a method include the SNuPE method.

Provided that the mutation results in an amino acid change (e.g., substitution, deletion or insertion) in the FLT3 protein, a sample prepared from the biological sample may be a protein. In such a case, a method using a molecule (e.g., an antibody) specifically binding to a site having the amino acid change ascribable to the mutation can be used for detecting the mutation.

Since the activating mutation of FLT3 elevates the phosphorylation level of FLT3, the activating mutation of FLT3 can also be detected by the quantification of phosphorylated FLT3. A phosphorylated protein measurement method known in the art can be used as a method for quantitatively measuring the phosphorylated FLT3 protein. For example, various methods using antibodies against the phosphorylated FLT3 protein can be utilized. Specific examples thereof can include Western blotting, immunoprecipitation, enzyme-linked immunosorbent assay (ELISA) and radioimmunoassay (RIA).

A humanized antibody, a mouse antibody, a rat antibody, a rabbit antibody, a sheep antibody or the like can be appropriately used as an antibody against the mutated FLT3 protein or the phosphorylated FLT3 protein as long as the antibody is directed to the mutated FLT3 protein or the phosphorylated FLT3 protein as an antigen and specifically binds to the antigen. The antibody may be a polyclonal antibody or may be a monoclonal antibody. A monoclonal antibody is preferred from the viewpoint that homogeneous antibodies can be stably produced. The polyclonal antibody and the monoclonal antibody can be prepared by methods well known to those skilled in the art. A desired antibody can also be selected, for use, from commercially available antibodies.

A hybridoma producing the monoclonal antibody can basically be prepared by use of a technique known in the art as follows: the antigen of interest or cells expressing the antigen of interest is used as a sensitizing antigen, and a desired animal is immunized with this sensitizing antigen according to a conventional immunization method. The obtained immunocytes are fused with known parent cells by a conventional cell fusion method. Then, cells producing the desired monoclonal antibody (hybridoma cells) can be selected by a conventional screening method. The preparation of the hybridoma can be carried out according to, for example, the method of Millstein ("Methods of Enzymology", 1981, Vol. 73, p. 3-46).

In this context, the phosphorylated FLT3 protein or a fragment thereof can be used as the antigen for preparing the monoclonal antibody. Those skilled in the art can easily obtain the phosphorylated FLT3 protein or the fragment thereof according to a method described in a book, for example, Sambrook ed., "Molecular Cloning: A Laboratory Manual", the 2nd edition, Vol. 1-3, Cold Spring Harbor Laboratory Press, NY, 1989.

The protein or the fragment thereof and the antibody may be immobilized on a support and used for quantifying the phosphorylated FLT3 protein. The support is not limited as long as the support permits immobilization of proteins. General examples thereof can include: inorganic materials such as glass plates, silicon wafers and resins; natural polymer materials including nitrocellulose; and synthetic polymer materials including nylon and polystyrene.

More specific examples of the method for detecting the activating mutation of FLT3 include a method for detecting a FLT3-ITD mutation described in WO9817808 and its corresponding U.S. Pat. No. 6,846,630 (WO9817808 and U.S. Pat. No. 6,846,630 are incorporated herein by reference in their entirety). This method can be performed by using a detection kit commercially available from Takara Bio Inc., etc.

A method of performing RT-PCR using mRNA obtained from the test subject-derived biological sample, followed by capillary electrophoresis can also be used as another similar method (Leukemia, 2005, 19, 1479-1482, which is incorporated herein by reference in its entirety).

Specific examples of the method for detecting the phosphorylated FLT3 protein include a method described in WO2010/054185 (which is incorporated herein by reference in its entirety).

From another viewpoint, cancer sensitive to an MDM2 inhibitor and that having wild-type TP53 are preferable as the types of the cancer to be treated.

Various approaches mentioned above as methods for confirming a mutation in FLT3 can be similarly utilized as methods for confirming TP53 to be wild-type. More specific examples thereof include a microarray method using a probe specific for a mutated DNA sequence (AmpliChip p53, Roche Molecular Systems, Inc., etc., http://www.ncbi.nlm-.nih.gov/pubmed/21319261), PCR using a probe specific for a mutated DNA sequence (qBiomarker Somatic Mutation PCR Arrays, Qiagen N.V., etc.), a method of reading the p53 gene sequence using a Sanger sequencer (http://p53.iarc.fr/Download/TP53_DirectSequencing_IARC.pdf), and a method of reading the p53 gene sequence using a next-generation sequencer (TruSeq Amplicon—Cancer Panel, Illumina http://www.illuminakk.co.jp/products/truseq_amplicon_cancer_panel.ilmn, Oncomine® Cancer Research Panel, Life Technologies Corp., http://www.lifetechnologies.com/jp/ja/home/clinical/preclinical-companion-diagnostic-development/oncomine-cancer-research-panel-workflow.html, etc.).

A method using a gene signature can also be preferably used as a method for predicting sensitivity to an MDM2 inhibitor. Examples of the gene signature for predicting sensitivity to an MDM2 inhibitor include, but are not particularly limited to, a gene group described in WO2014/020502 (WO2014/020502 is incorporated herein by reference in its entirety). More specifically, a gene group comprising at least one gene selected from the group consisting of MDM2, CDKN1A, ZMAT3, DDB2, FDXR, RPS27L, BAX, RPM2B, SESN1, CCNG1, XPC, TNFSF10B and AEN (the gene group may comprise all of these genes) can be preferably used. Other examples thereof include a gene group described in WO2015/000945 (WO2014/000945 is incorporated herein by reference in its entirety). More specifically, a gene group comprising at least one gene selected from the group consisting of BAX, RPS27L, EDA2R, XPC, DDB2, FDXR, MDM2, CDKN1A, TRIAP1, BBC3, CCNG1, TNFRSF10B and CDKN2A (the gene group may comprise all of these genes) can be preferably used. The number of genes contained in the gene group is not limited. A sensitive signature that allows the cancer to be confirmed as sensitive to an MDM2 inhibitor when the gene contained in the gene signature is highly expressed can be preferably used.

The medicament according to the present invention may be used in combination with an additional anti-tumor agent. Examples thereof include anti-tumor antibiotics, anti-tumor plant constituents, BRMs (biological response modifiers), hormones, vitamins, anti-tumor antibodies, molecular target drugs, alkylating agents, metabolic antagonists and other anti-tumor agents.

More specifically, examples of alkylating agents include: alkylating agents such as nitrogen mustard, nitrogen mustard N-oxide, bendamustine and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin and ranimustine; and busulfan, improsulfan tosylate, temozolomide and dacarbazine.

Various examples of metabolic antagonists include: purine metabolic antagonists such as 6-mercaptopurine, 6-thioguanine and thioinosine; pyrimidine metabolic antagonists such as fluorouracil, tegafur, tegafur-uracil, carmofur, doxifluridine, broxuridine, cytarabine and enocitabine; and folic acid metabolic antagonists such as methotrexate and trimetrexate.

Examples of anti-tumor antibiotics include: mitomycin C, bleomycin, peplomycin, daunorubicin, aclarubicin, doxorubicin, idarubicin, pirarubicin, THP-adriamycin, 4'-epidoxorubicin and epirubicin; and chromomycin A3 and actinomycin D.

Examples of anti-tumor plant constituents and their derivatives include: vinca alkaloids such as vindesine, vincristine and vinblastine; taxanes such as paclitaxel, docetaxel and cabazitaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, mepitiostane and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, ipilimumab, nivolumab, pembrolizumab, avelumab, pidilizumab, atezolizumab, ramucirumab, imatinib mesylate, dasatinib, gefitinib, erlotinib, osimertinib, sunitinib, lapatinib, dabrafenib, trametinib, cobimetinib, pazopanib, palbociclib, panobinostat, sorafenib, crizotinib, vemurafenib, ibrutinib, bortezomib, carfilzomib, ixazomib and gilteritinib.

Examples of other anti-tumor agents include cisplatin, carboplatin, oxaliplatin, tamoxifen, letrozole, anastrozole, exemestane, toremifene citrate, fulvestrant, bicalutamide, flutamide, mitotane, leuprorelin, goserelin acetate, camptothecin, ifosfamide, cyclophosphamide, melphalan, L-asparaginase, aceglatone, sizofiran, picibanil, procarbazine, pipobroman, neocarzinostatin, hydroxyurea, ubenimex, azacitidine, decitabine, thalidomide, lenalidomide, pomalidomide, eribulin, tretinoin and krestin.

Another aspect of the present invention relates to a method for predicting responsiveness to treatment of cancer with (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof in combination, comprising using a test subject-derived biological sample, detecting the presence or absence of an activating mutation of FLT3 contained in the biological sample, and confirming the test subject having the detected activating mutation of FLT3 to be responsive to the treatment of cancer with the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof in combination.

An alternative aspect of the present invention relates to a method for selecting a subject for treatment of cancer with (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof in combination, comprising using a test subject-derived biological sample, detecting the presence or absence of an activating mutation of FLT3 in the biological sample, and selecting the test subject having the detected activating mutation of FLT3 as the subject for the treatment of cancer with the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof in combination.

The present invention further relates to a method for predicting responsiveness to treatment of cancer or a method for selecting a subject for treatment of cancer, wherein the activating mutation of FLT3 is a FLT3-ITD mutation.

A method for collecting the test subject-derived biological sample and a method for detecting the activating mutation of FLT3 or the FLT3-ITD mutation in the biological sample are as mentioned above.

EXAMPLES

Hereinafter, the present invention will be specifically explained with reference to the Examples given below. However, the present invention is not limited to these examples, and they should not be construed in any limitative way.

Test Example 1 Study on In Vivo Effect of Combined Use of Compound A and Quizartinib Human acute myeloid leukemia cell line MOLM-13 cells having a FLT3-ITD mutation and wild-type TP53 were suspended to $5 \times 10^7$ cells/mL using phosphate-buffered saline. 0.1 mL of the prepared cell suspension was subcutaneously transplanted to each NOD-SCID mouse (male, 5 to 7 weeks old). On 6 days after the tumor inoculation, after confirmation that the average tumor volume exceeded 100 mm³, the mice were randomized (N=6/group) on the basis of their tumor volume values. 25 mg/kg or 50 mg/kg Compound A or 0.5 mg/kg or 1 mg/kg quizartinib (LC Laboratories) was administered by oral gavage to the mice. For a combined use group, 25 mg/kg or 50 mg/kg Compound A and 0.5 mg/kg or 1 mg/kg quizartinib were orally administered sequentially by forced administration. The administration was performed once a day for 5 consecutive days (6 to 10 days after the tumor inoculation) from the date of randomization (6 days after the tumor inoculation), and after a 2-day drug holiday, performed once a day for 4 consecutive days (13 to 16 days after the tumor inoculation). The length (mm) and width (mm) of tumor were measured over time using an electronic digital caliper. Tumor growth inhibition % (TGI %) on the date of assessment (17 days after the tumor inoculation) calculated according to calculation formula (4) shown below was used in evaluation. Also, the body weights were measured over time using an automatic balance for small animals, and body weight change % was calculated according to calculation formula (5) shown below to assess the influence of drug administration on the body weights. In addition, the results of the last body weight measurement were used in dose calculation.

$$\text{TGI (\%)} = (1 - A/B) \times 100 \quad (4)$$

A: Average tumor volume of the compound-administered group on the date of assessment (*)

B: Average tumor volume of the untreated control group on the date of assessment (*)

*: The tumor volume was calculated according to ½× [Major axis of tumor]×[Minor axis of tumor]×[Minor axis of tumor].

Body weight change (%)=Average body weight change % of the individuals $$\text{Body weight change \% of each individual} = (1 - BWn/BWs) \times 100 \quad (5)$$

BWn: Body weight on day n
BWs: Body weight on the start day of administration
The results are shown in FIG. 1 and Tables 1 to 3.

TABLE 1

| Group | TGI (%) |
|---|---|
| Compound A 25 mg/kg | 38 |
| Compound A 50 mg/kg | 82 |
| Compound A 25 mg/kg + Quizartinib 0.5 mg/kg | 57 |
| Compound A 50 mg/kg + Quizartinib 0.5 mg/kg | 85 |
| Compound A 25 mg/kg + Quizartinib 1 mg/kg | 85 |
| Compound A 50 mg/kg + Quizartinib 1 mg/kg | 97 |
| Quizartinib 0.5 mg/kg | 29 |
| Quizartinib 1 mg/kg | 61 |

TABLE 2

Estimated tumor volume (mm³)

| Group (N = 6) | | Days after tumor inoculation | | | | | |
|---|---|---|---|---|---|---|---|
| | | 6 | 8 | 10 | 13 | 15 | 17 |
| 1. Untreated | average | 163 | 302 | 625 | 1227 | 1667 | 2667 |
| | SE | 12 | 39 | 64 | 136 | 152 | 195 |
| 2. DS-3032b 25 mg/kg | average | 169 | 266 | 425 | 812 | 983 | 1661 |
| | SE | 14 | 24 | 41 | 78 | 63 | 104 |
| 3. DS-3032b 50 mg/kg | average | 162 | 195 | 210 | 325 | 375 | 467 |
| | SE | 12 | 15 | 23 | 37 | 49 | 64 |
| 4. DS-3032b 25 mg/kg + Quizartinib 0.5 mg/kg | average | 169 | 168 | 220 | 673 | 753 | 1149 |
| | SE | 14 | 10 | 21 | 50 | 66 | 83 |
| 5. DS-3032b 50 mg/kg + Quizartinib 0.5 mg/kg | average | 164 | 134 | 106 | 290 | 297 | 387 |
| | SE | 13 | 12 | 11 | 37 | 47 | 81 |
| 6. DS-3032b 25 mg/kg + Quizartinib 1 mg/kg | average | 165 | 132 | 98 | 314 | 318 | 387 |
| | SE | 12 | 12 | 11 | 45 | 40 | 43 |
| 7. DS-3032b 50 mg/kg + Quizartinib 1 mg/kg | average | 171 | 111 | 62 | 116 | 96 | 67 |
| | SE | 15 | 8 | 7 | 18 | 17 | 14 |
| 8. Quizartinib 0.5 mg/kg | average | 167 | 239 | 477 | 897 | 1212 | 1893 |
| | SE | 13 | 28 | 36 | 61 | 96 | 154 |
| 9. Quizartinib 1 mg/kg | average | 163 | 168 | 203 | 593 | 663 | 1039 |
| | SE | 13 | 11 | 18 | 39 | 57 | 67 |

TABLE 3

Body weight change (%)

| Group (N = 6) | | Days after tumor inoculation | | | | | |
|---|---|---|---|---|---|---|---|
| | | 6 | 8 | 10 | 13 | 15 | 17 |
| 1. Untreated | average | 0.0 | 2.6 | 6.0 | 10.8 | 15.2 | 19.2 |
| | SD | 0.0 | 1.2 | 1.3 | 1.0 | 2.0 | 2.8 |
| 2. DS-3032b 25 mg/kg | average | 0.0 | 2.1 | 3.1 | 6.4 | 8.0 | 10.6 |
| | SD | 0.0 | 1.1 | 1.9 | 1.9 | 2.5 | 2.7 |
| 3. DS-3032b 50 mg/kg | average | 0.0 | 1.5 | 2.7 | 5.5 | 6.8 | 5.8 |
| | SD | 0.0 | 1.4 | 2.3 | 2.5 | 3.5 | 3.4 |

TABLE 3-continued

| | | Body weight change (%) | | | | | |
|---|---|---|---|---|---|---|---|
| | | Days after tumor inoculation | | | | | |
| Group (N = 6) | | 6 | 8 | 10 | 13 | 15 | 17 |
| 4. DS-3032b 25 mg/kg + Quizartinib 0.5 mg/kg | average | 0.0 | 0.3 | 1.4 | 5.1 | 5.5 | 6.1 |
| | SD | 0.0 | 2.1 | 2.9 | 3.1 | 4.1 | 4.2 |
| 5. DS-3032b 50 mg/kg + Quizartinib 0.5 mg/kg | average | 0.0 | 1.0 | 0.3 | 2.9 | 4.2 | 3.6 |
| | SD | 0.0 | 2.0 | 3.1 | 3.8 | 4.6 | 4.2 |
| 6. DS-3032b 25 mg/kg + Quizartinib 1 mg/kg | average | 0.0 | 1.1 | 0.7 | 4.7 | 2.8 | 3.3 |
| | SD | 0.0 | 2.4 | 3.7 | 2.8 | 4.1 | 4.5 |
| 7. DS-3032b 50 mg/kg + Quizartinib 1 mg/kg | average | 0.0 | −0.6 | −0.3 | 2.5 | 2.6 | 3.2 |
| | SD | 0.0 | 2.6 | 4.8 | 3.3 | 5.3 | 5.1 |
| 8. Quizartinib 0.5 mg/kg | average | 0.0 | 4.2 | 4.2 | 8.5 | 9.6 | 10.7 |
| | SD | 0.0 | 2.9 | 2.6 | 2.1 | 1.6 | 2.8 |
| 9. Quizartinib 1 mg/kg | average | 0.0 | 0.2 | 1.8 | 4.6 | 5.1 | 5.8 |
| | SD | 0.0 | 1.7 | 1.9 | 3.2 | 3.4 | 3.0 |

Free Text of Sequence Listing
SEQ ID NO: 1: FLT3 mRNA encoding FLT3 protein (SEQ ID NO: 2).
SEQ ID NO: 2: Amino acid sequence of the FLT3 protein.
SEQ ID NO: 3: TP53 mRNA encoding TP53 protein (SEQ ID NO: 4).
SEQ ID NO: 4: Amino acid sequence of the TP53 protein.

The invention claimed is:

1. A method of treating cancer comprising administering (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or a pharmaceutically acceptable salt thereof and N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof in combination,
    wherein the cancer is acute myeloid leukemia (AML) having a FLT3-ITD mutation and wild-type TP53.

2. The method of claim 1, wherein the respective salts of the compounds are (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydro-dispiro[cyclohexane-1,2'-pyrrolidine-3',3"-indole]-5'-carboxamide p-toluenesulfonate and N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride.

3. The method of claim 1, wherein the cancer is cancer determined to be MDM2 inhibitor-sensitive using a gene signature.

4. The method of claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol-2-yl]phenyl}urea or the pharmaceutically acceptable salt thereof are administered at the same time.

5. The method of claim 1, wherein the (3'R,4'S,5'R)—N-[(3R,6S)-6-carbamoyltetrahydro-2H-pyran-3-yl]-6"-chloro-4'-(2-chloro-3-fluoropyridin-4-yl)-4,4-dimethyl-2"-oxo-1",2"-dihydrodispiro[cyclohexane-1,2'-pyrrolidine-3',3"-indole]-5'-carboxamide or the pharmaceutically acceptable salt thereof and the N-(5-tert-butyl-isoxazol-3-yl)-N'-{4-[7-(2-morpholin-4-yl-ethoxy)imidazo[2,1-b][1,3]benzothiazol- 2-yl]phenyl}urea or the pharmaceutically acceptable salt thereof are administered at different times.

\* \* \* \* \*

UNITED STATES PATENT AND TRADEMARK OFFICE
CERTIFICATE OF CORRECTION

Page 1 of 1

PATENT NO. : 10,716,790 B2
APPLICATION NO. : 15/487738
DATED : July 21, 2020
INVENTOR(S) : Seki It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 14 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*